(12) United States Patent
Blair et al.

(10) Patent No.: US 8,710,957 B2
(45) Date of Patent: Apr. 29, 2014

(54) METHOD, APPARATUS AND ARTICLE FOR DETECTION OF TRANSPONDER TAGGED OBJECTS, FOR EXAMPLE DURING SURGERY

(75) Inventors: William A. Blair, San Diego, CA (US); Bruce E. Barnes, Escondido, CA (US); David A. Poirier, Escondido, CA (US)

(73) Assignee: RF Surgical Systems, Inc., Bellevue, WA (US)

( * ) Notice: Subject to any disclaimer, the term of this patent is extended or adjusted under 35 U.S.C. 154(b) by 1091 days.

(21) Appl. No.: 12/038,593

(22) Filed: Feb. 27, 2008

(65) Prior Publication Data

US 2008/0204245 A1    Aug. 28, 2008

Related U.S. Application Data

(60) Provisional application No. 60/892,208, filed on Feb. 28, 2007.

(51) Int. Cl.
*G08B 13/14*    (2006.01)

(52) U.S. Cl.
USPC .... 340/10.1; 340/10.3; 340/572.1; 340/572.3

(58) Field of Classification Search
CPC ........................................ G08B 13/14
USPC ................ 340/10.1, 10.3, 10.4, 572.1, 572.4, 340/572.7
See application file for complete search history.

(56) References Cited

U.S. PATENT DOCUMENTS

| | | | |
|---|---|---|---|
| 2,740,405 | A | 4/1956 | Riordan |
| 3,031,864 | A | 5/1962 | Freundlich |
| 3,422,816 | A | 1/1969 | Robinson et al. |
| 3,587,583 | A | 6/1971 | Greenberg |
| 4,034,297 | A | 7/1977 | Giorgi et al. |
| 4,114,601 | A | 9/1978 | Abels |
| 4,193,405 | A | 3/1980 | Abels |
| 4,422,548 | A | 12/1983 | Cheesman et al. |
| D272,943 | S | 3/1984 | Stone et al. |
| 4,477,256 | A | 10/1984 | Hirsch |
| 4,540,398 | A | 9/1985 | Barson et al. |
| 4,626,251 | A | 12/1986 | Shen |
| 4,636,208 | A | 1/1987 | Rath |
| 4,639,253 | A | 1/1987 | Dyer et al. |
| 4,645,499 | A | 2/1987 | Rupinskas |
| 4,658,818 | A | 4/1987 | Miller, Jr. et al. |

(Continued)

FOREIGN PATENT DOCUMENTS

| | | |
|---|---|---|
| AU | 199852698 B2 | 3/1993 |
| AU | 2003249257 A1 | 2/2004 |

(Continued)

OTHER PUBLICATIONS

U.S. Appl. No. 60/811,376, filed Jun. 6, 2006, Blair et al.

(Continued)

*Primary Examiner* — Edwin Holloway, III
(74) *Attorney, Agent, or Firm* — Seed IP Law Group PLLC

(57) ABSTRACT

A system determines the presence or absence of objects by interrogating or exciting transponders coupled to the objects using pulsed signals over a number of wide band frequency bands with dynamic tuning about a center frequency of each band and less sensitivity to noise fluctuation.

35 Claims, 18 Drawing Sheets

(56) References Cited

U.S. PATENT DOCUMENTS

| | | | |
|---|---|---|---|
| 4,681,111 | A | 7/1987 | Silvian |
| 4,704,109 | A | 11/1987 | Rupinskas |
| 4,718,897 | A | 1/1988 | Elves |
| 4,893,118 | A | 1/1990 | Lewiner et al. |
| 4,917,694 | A | 4/1990 | Jessup |
| 4,935,019 | A | 6/1990 | Papp, Jr. |
| 4,938,901 | A | 7/1990 | Groitzsch et al. |
| 4,992,675 | A | 2/1991 | Conner, Jr. et al. |
| 5,031,642 | A | 7/1991 | Nosek |
| 5,041,103 | A | 8/1991 | Rupinskas |
| 5,045,080 | A | 9/1991 | Dyer et al. |
| 5,049,219 | A | 9/1991 | Johns et al. |
| 5,057,095 | A | 10/1991 | Fabian |
| 5,105,829 | A | 4/1992 | Fabian et al. |
| 5,107,862 | A | 4/1992 | Fabian et al. |
| 5,112,325 | A | 5/1992 | Zachry |
| D330,872 | S | 11/1992 | Ball |
| 5,181,021 | A | 1/1993 | Lee et al. |
| 5,188,126 | A | 2/1993 | Fabian et al. |
| 5,190,059 | A | 3/1993 | Fabian et al. |
| 5,224,593 | A | 7/1993 | Bennett |
| 5,235,326 | A | 8/1993 | Beigel et al. |
| 5,258,742 | A | 11/1993 | Soldevila Domingo et al. |
| 5,329,944 | A | 7/1994 | Fabian et al. |
| 5,353,011 | A | 10/1994 | Wheeler et al. |
| D353,343 | S | 12/1994 | Eberhardt |
| D354,927 | S | 1/1995 | Andrau |
| D356,052 | S | 3/1995 | Andrau |
| D359,705 | S | 6/1995 | Ball |
| 5,446,447 | A | 8/1995 | Carney et al. ............... 340/572 |
| 5,450,622 | A | 9/1995 | Vandegraaf |
| 5,456,718 | A | 10/1995 | Szymaitis |
| 5,482,036 | A | 1/1996 | Diab et al. ............... 128/633 |
| 5,575,781 | A | 11/1996 | DeBusk |
| 5,629,498 | A | 5/1997 | Pollock et al. |
| 5,650,596 | A | 7/1997 | Morris et al. |
| 5,664,582 | A | 9/1997 | Szymaitis |
| 5,725,517 | A | 3/1998 | DeBusk |
| 5,792,128 | A | 8/1998 | DeBusk |
| D412,135 | S | 7/1999 | Saito |
| 5,923,001 | A | 7/1999 | Morris et al. |
| 5,928,151 | A | 7/1999 | Hossack et al. |
| 5,931,824 | A | 8/1999 | Stewart et al. |
| 5,963,132 | A | 10/1999 | Yoakum |
| 5,969,613 | A | 10/1999 | Yeager et al. |
| D418,773 | S | 1/2000 | Saito |
| 6,026,818 | A | 2/2000 | Blair et al. ............... 128/899 |
| D423,673 | S | 4/2000 | Bassøe |
| 6,075,797 | A | 6/2000 | Thomas |
| 6,093,869 | A | 7/2000 | Roe et al. |
| 6,172,608 | B1 | 1/2001 | Cole |
| 6,201,469 | B1* | 3/2001 | Balch et al. ............... 340/10.1 |
| 6,211,666 | B1 | 4/2001 | Acker |
| 6,215,437 | B1 | 4/2001 | Schürmann et al. |
| 6,223,137 | B1 | 4/2001 | McCay et al. |
| 6,232,878 | B1 | 5/2001 | Rubin |
| 6,270,460 | B1 | 8/2001 | McCartan et al. |
| 6,276,033 | B1 | 8/2001 | Johnson et al. |
| 6,317,027 | B1 | 11/2001 | Watkins |
| 6,349,234 | B2 | 2/2002 | Pauly et al. |
| 6,353,406 | B1* | 3/2002 | Lanzl et al. ............... 342/118 |
| 6,359,562 | B2 | 3/2002 | Rubin |
| 6,366,206 | B1 | 4/2002 | Ishikawa et al. |
| D456,907 | S | 5/2002 | Sanfilippo |
| 6,384,296 | B1 | 5/2002 | Roe et al. |
| 6,401,722 | B1 | 6/2002 | Krag |
| 6,441,741 | B1 | 8/2002 | Yoakum |
| D471,281 | S | 3/2003 | Baura et al. |
| 6,557,752 | B1 | 5/2003 | Yacoob |
| 6,566,997 | B1* | 5/2003 | Bradin ............... 340/10.2 |
| 6,588,661 | B2 | 7/2003 | Degrauwe et al. |
| 6,632,216 | B2 | 10/2003 | Houzego et al. |
| 6,633,226 | B1 | 10/2003 | Nysen |
| 6,641,039 | B2 | 11/2003 | Southard |
| 6,648,223 | B2 | 11/2003 | Boukhny et al. |
| 6,650,240 | B2 | 11/2003 | Lee et al. |
| 6,654,629 | B2 | 11/2003 | Montegrande |
| 6,696,954 | B2 | 2/2004 | Chung |
| 6,722,783 | B2 | 4/2004 | Jackson, Sr. |
| 6,734,795 | B2 | 5/2004 | Price |
| 6,744,378 | B1 | 6/2004 | Tyburski |
| 6,753,783 | B2 | 6/2004 | Friedman et al. |
| D495,055 | S | 8/2004 | Silber |
| 6,774,800 | B2 | 8/2004 | Friedman et al. |
| 6,777,623 | B2 | 8/2004 | Ballard |
| 6,778,089 | B2 | 8/2004 | Yoakum |
| 6,786,405 | B2 | 9/2004 | Wiedenhoefer |
| 6,812,824 | B1 | 11/2004 | Goldinger et al. |
| 6,812,842 | B2 | 11/2004 | Dimmer |
| 6,822,570 | B2 | 11/2004 | Dimmer et al. |
| 6,838,990 | B2 | 1/2005 | Dimmer |
| D502,419 | S | 3/2005 | Copen |
| 6,861,954 | B2 | 3/2005 | Levin |
| 6,879,300 | B2 | 4/2005 | Rochelle et al. |
| 6,909,366 | B1 | 6/2005 | Marsh et al. |
| 6,977,504 | B2 | 12/2005 | Wright et al. |
| 6,998,541 | B2 | 2/2006 | Morris et al. |
| 7,001,366 | B2 | 2/2006 | Ballard |
| 7,019,650 | B2 | 3/2006 | Volpi et al. |
| 7,026,924 | B2 | 4/2006 | Degrauwe et al. |
| 7,026,927 | B2 | 4/2006 | Wright et al. |
| 7,037,336 | B2 | 5/2006 | Ward |
| D526,586 | S | 8/2006 | McCaghren et al. |
| 7,098,793 | B2 | 8/2006 | Chung |
| 7,098,866 | B2 | 8/2006 | Desjeux et al. |
| 7,118,029 | B2 | 10/2006 | Nycz et al. |
| 7,135,973 | B2 | 11/2006 | Kittel et al. |
| 7,135,978 | B2 | 11/2006 | Gisselberg et al. |
| 7,142,118 | B2 | 11/2006 | Hamilton et al. |
| 7,142,815 | B2 | 11/2006 | Desjeux et al. |
| D534,448 | S | 1/2007 | Shaffer, II et al. |
| 7,158,030 | B2 | 1/2007 | Chung |
| 7,158,754 | B2 | 1/2007 | Anderson |
| 7,160,258 | B2 | 1/2007 | Imran et al. |
| D536,673 | S | 2/2007 | Silber |
| 7,176,798 | B2 | 2/2007 | Dimmer et al. |
| 7,183,914 | B2 | 2/2007 | Norman et al. |
| 7,183,927 | B2 | 2/2007 | Kolton et al. |
| 7,245,893 | B1 | 7/2007 | Husted et al. |
| 7,256,695 | B2 | 8/2007 | Hamel et al. |
| 7,256,696 | B2 | 8/2007 | Levin |
| 7,268,684 | B2 | 9/2007 | Tethrake et al. |
| 7,299,981 | B2 | 11/2007 | Hickle et al. |
| D557,421 | S | 12/2007 | Fleck et al. |
| D558,352 | S | 12/2007 | Sanfilippo |
| 7,307,530 | B2 | 12/2007 | Fabian et al. |
| D558,882 | S | 1/2008 | Brady |
| 7,319,396 | B2 | 1/2008 | Homanfar et al. |
| 7,319,397 | B2 | 1/2008 | Chung et al. |
| 7,325,723 | B2 | 2/2008 | Desjeux |
| 7,333,013 | B2 | 2/2008 | Berger |
| 7,342,497 | B2 | 3/2008 | Chung et al. |
| 7,362,228 | B2 | 4/2008 | Nycz et al. |
| D568,186 | S | 5/2008 | Blair et al. |
| 7,382,255 | B2 | 6/2008 | Chung |
| 7,397,364 | B2 | 7/2008 | Govari |
| 7,399,899 | B2 | 7/2008 | Fabian |
| 7,408,168 | B1 | 8/2008 | Aufrichtig et al. |
| 7,420,468 | B2 | 9/2008 | Fabian et al. |
| 7,423,535 | B2 | 9/2008 | Chung et al. |
| 7,446,646 | B2 | 11/2008 | Huomo |
| 7,449,614 | B2 | 11/2008 | Ales, III |
| 7,464,713 | B2 | 12/2008 | Fabian et al. |
| 7,465,847 | B2 | 12/2008 | Fabian |
| D584,414 | S | 1/2009 | Lash et al. |
| 7,474,222 | B2 | 1/2009 | Yang et al. |
| 7,492,257 | B2 | 2/2009 | Tethrake et al. |
| 7,492,263 | B2 | 2/2009 | Marsilio et al. |
| 7,508,308 | B2 | 3/2009 | Chung |
| D590,342 | S | 4/2009 | Dávila et al. |
| 7,513,425 | B2 | 4/2009 | Chung |
| D598,114 | S | 8/2009 | Cryan |
| 7,696,877 | B2 | 4/2010 | Barnes et al. |
| 7,769,422 | B2 | 8/2010 | DiSilvestro et al. |

(56) References Cited

U.S. PATENT DOCUMENTS

| | | |
|---|---|---|
| 7,855,656 B2 | 12/2010 | Maschke |
| 7,876,097 B2 | 1/2011 | Greim |
| 7,898,420 B2 | 3/2011 | Blair et al. |
| 8,111,162 B2 | 2/2012 | Barnes et al. |
| 2001/0030610 A1 | 10/2001 | Rochelle et al. |
| 2002/0011932 A1* | 1/2002 | Rodgers et al. ............ 340/572.1 |
| 2002/0032435 A1 | 3/2002 | Levin |
| 2002/0070863 A1 | 6/2002 | Brooking |
| 2002/0143320 A1 | 10/2002 | Levin |
| 2002/0165587 A1 | 11/2002 | Zhang et al. |
| 2002/0188259 A1 | 12/2002 | Hickle et al. |
| 2003/0004411 A1 | 1/2003 | Govari et al. |
| 2003/0052788 A1 | 3/2003 | Kwong-Tai Chung |
| 2003/0105394 A1 | 6/2003 | Fabian et al. |
| 2004/0008123 A1 | 1/2004 | Carrender et al. |
| 2004/0129279 A1 | 7/2004 | Fabian et al. |
| 2004/0137844 A1 | 7/2004 | Desjeux et al. |
| 2004/0138554 A1 | 7/2004 | Dimmer et al. |
| 2004/0250819 A1 | 12/2004 | Blair et al. ............... 128/899 |
| 2004/0254420 A1 | 12/2004 | Ward |
| 2005/0049564 A1 | 3/2005 | Fabian |
| 2005/0110640 A1 | 5/2005 | Chung |
| 2005/0131397 A1 | 6/2005 | Levin |
| 2005/0154293 A1 | 7/2005 | Gisselberg et al. |
| 2005/0212673 A1 | 9/2005 | Forster |
| 2005/0247794 A1 | 11/2005 | Jones et al. |
| 2005/0249036 A1 | 11/2005 | Davies et al. |
| 2005/0267550 A1 | 12/2005 | Hess et al. |
| 2006/0055537 A1 | 3/2006 | Jackson |
| 2006/0084934 A1 | 4/2006 | Frank |
| 2006/0106368 A1 | 5/2006 | Miller et al. |
| 2006/0109086 A1 | 5/2006 | Amtmann |
| 2006/0187044 A1 | 8/2006 | Fabian et al. |
| 2006/0194899 A1 | 8/2006 | Ohashi et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0244597 A1 | 11/2006 | Tethrake et al. |
| 2006/0244652 A1 | 11/2006 | Tethrake et al. |
| 2006/0270933 A1 | 11/2006 | Benson et al. |
| 2007/0004994 A1 | 1/2007 | Sherman |
| 2007/0005141 A1 | 1/2007 | Sherman |
| 2007/0034670 A1 | 2/2007 | Racenet et al. |
| 2007/0038233 A1 | 2/2007 | Martinez et al. |
| 2007/0055109 A1 | 3/2007 | Bass et al. |
| 2007/0109099 A1 | 5/2007 | Raphaeli et al. |
| 2007/0125392 A1 | 6/2007 | Olson, Jr. et al. |
| 2007/0152823 A1 | 7/2007 | Hirahara et al. |
| 2007/0209957 A1 | 9/2007 | Glenn et al. |
| 2007/0216062 A1 | 9/2007 | Frank |
| 2007/0219516 A1 | 9/2007 | Patel et al. |
| 2007/0238982 A1 | 10/2007 | Caylor, III |
| 2007/0239289 A1 | 10/2007 | Cambre et al. |
| 2007/0244470 A1 | 10/2007 | Barker, Jr. et al. |
| 2007/0265690 A1 | 11/2007 | Lichtenstein et al. |
| 2007/0270660 A1 | 11/2007 | Caylor, III et al. |
| 2007/0285249 A1 | 12/2007 | Blair et al. |
| 2008/0007411 A1 | 1/2008 | Levin |
| 2008/0021308 A1 | 1/2008 | Dimmer et al. |
| 2008/0030303 A1 | 2/2008 | Kobren et al. |
| 2008/0051746 A1 | 2/2008 | Shen-Gunther |
| 2008/0126122 A1 | 5/2008 | Warner et al. |
| 2008/0132860 A1 | 6/2008 | Smith et al. |
| 2008/0231452 A1 | 9/2008 | Levin |
| 2008/0237341 A1 | 10/2008 | Fleck et al. |
| 2008/0243404 A1 | 10/2008 | Banhegyesi |
| 2008/0272913 A1 | 11/2008 | Barnes et al. |
| 2008/0281190 A1 | 11/2008 | Petcavich et al. |
| 2008/0296373 A1 | 12/2008 | Zmood et al. |
| 2009/0014518 A1 | 1/2009 | Stewart et al. |
| 2009/0315681 A1 | 12/2009 | Blair |
| 2010/0033309 A1 | 2/2010 | Blair |
| 2010/0108079 A1 | 5/2010 | Blair |
| 2010/0109848 A1 | 5/2010 | Blair et al. |
| 2011/0181394 A1 | 7/2011 | Blair |

FOREIGN PATENT DOCUMENTS

| | | |
|---|---|---|
| CN | 101460096 A | 6/2009 |
| EP | 1 612 554 A1 | 1/2006 |
| EP | 2 087 850 A2 | 8/2009 |
| JP | 2009539478 A | 11/2009 |
| WO | 02/33917 A1 | 5/2002 |
| WO | 2004/008387 A1 | 1/2004 |
| WO | 2004/086997 A1 | 10/2004 |
| WO | 2006/060781 A1 | 6/2006 |
| WO | 2007/146091 A1 | 12/2007 |
| WO | 2008/024921 A1 | 2/2008 |
| WO | 2008/112709 A1 | 9/2008 |
| WO | 2008/133634 A1 | 11/2008 |
| WO | 2009/151946 A1 | 12/2009 |
| WO | 2009/154987 A1 | 12/2009 |

OTHER PUBLICATIONS

Barnes et al., "Design for a FET Based 1 MHz, 10 kV Pulse Generator," Pulsed Power Conference, Digest of Technical Papers, Tenth IEEE International, 2:1335-1340, 1995.

Clearcount Medical Solutions, "The SmartSponge System," Downloaded from http://clearcount.com on Oct. 20, 2009, 7 pages.

Macario et al., "Initial Clinical Evaluation of a Handheld Device for Detecting Retained Surgical Gauze Sponges Using Radiofrequency Identification Technology," Arch Surg 141:659-662, Jul. 2006.

International Search Report, mailed Jan. 4, 2010, for PCT/US2009/045312, 3 pages.

Written Opinion, mailed Jan. 4, 2010, for PCT/US2009/045312, 3 pages.

Blair et al., "Tag and Detection Device," U.S. Appl. No. 60/458,222, filed Mar. 27, 2003, 23 pages.

Blair et al., "Transponder Housing and Device to Mark Implements, Such As Surgical Implements, and Method of Using Same," U.S. Appl. No. 60/894,435, filed Mar. 12, 2007, 30 pages.

Blair, "Apparatus, Method, and Article for Detection and Identification of Multi-Mode Integral Transponder Tagged Objects," U.S. Appl. No. 61/056,229, filed May 27, 2008, 38 pages.

Barnes et al., "Method, Apparatus and Article for Detection of Transponder Tagged Objects, for Example During Surgery," U.S. Appl. No. 61/056,787, filed May 28, 2008, 60 pages.

Blair, "Transponder Device to Mark Implements, Such As Surgical Implements, and Method of Manufacturing and Using Same," U.S. Appl. No. 61/086,727, filed Aug. 6, 2008, 30 pages.

Barnes et al., "Method, Apparatus and Article for Detection of Transponder Tagged Objects, for Example During Surgery," U.S. Appl. No. 61/091,667, filed Aug. 25, 2008, 76 pages.

Blair, "Multi-Modal Transponder and Method and Apparatus to Detect Same," U.S. Appl. No. 61/102,749, filed Oct. 3, 2008, 48 pages.

Blair et al., "Method and Apparatus to Detect Transponder Tagged Objects, for Example During Surgery," U.S. Appl. No. 61/109,104, filed Oct. 28, 2008, 73 pages.

Blair, "Detectable Surgical Objects and Methods of Making Same," U.S. Appl. No. 61/109,142, filed Oct. 28, 2008, 47 pages.

Blair et al., "Method and Apparatus to Detect Transponder Tagged Objects, for Example During Medical Procedures," U.S. Appl. No. 61/242,704, filed Sep. 15, 2009, 127 pages.

Blair, "Transponder Device to Mark Implements, Such As Surgical Implements, and Method of Manufacturing and Using Same," U.S. Appl. No. 61/220,452, filed Jun. 25, 2009, 46 pages.

Blair, "Radio Opaque Device with Resonant Nanostructures," U.S. Appl. No. 61/163,813, filed Mar. 26, 2009, 47 pages.

Blair et al., "Method and Apparatus to Detect Transponder Tagged Objects, for Example During Surgery," U.S. Appl. No. 61/222,443, filed Jul. 1, 2009, 95 pages.

Blair, "Method and Apparatus to Account for Transponder Tagged Objects Used During Medical Procedures," U.S. Appl. No. 61/263,726, filed Nov. 23, 2009, 78 pages.

(56) References Cited

OTHER PUBLICATIONS

Blair, "Transponder Housing," U.S. Appl. No. 29/322,539, filed Aug. 6, 2008, 6 pages.
Blair, "Attachment Article to Attach a Transponder to a Surgical Sponge," U.S. Appl. No. 29/336,007, filed Apr. 27, 2009, 4 pages.
Blair, "Attachment Article to Attach a Transponder to a Surgical Sponge," U.S. Appl. No. 29/336,008, filed Apr. 27, 2009, 7 pages.
Blair, "Article to Attach a Transponder to a Surgical Sponge," U.S. Appl. No. 29/336,009, filed Apr. 27, 2009, 4 pages.

* cited by examiner

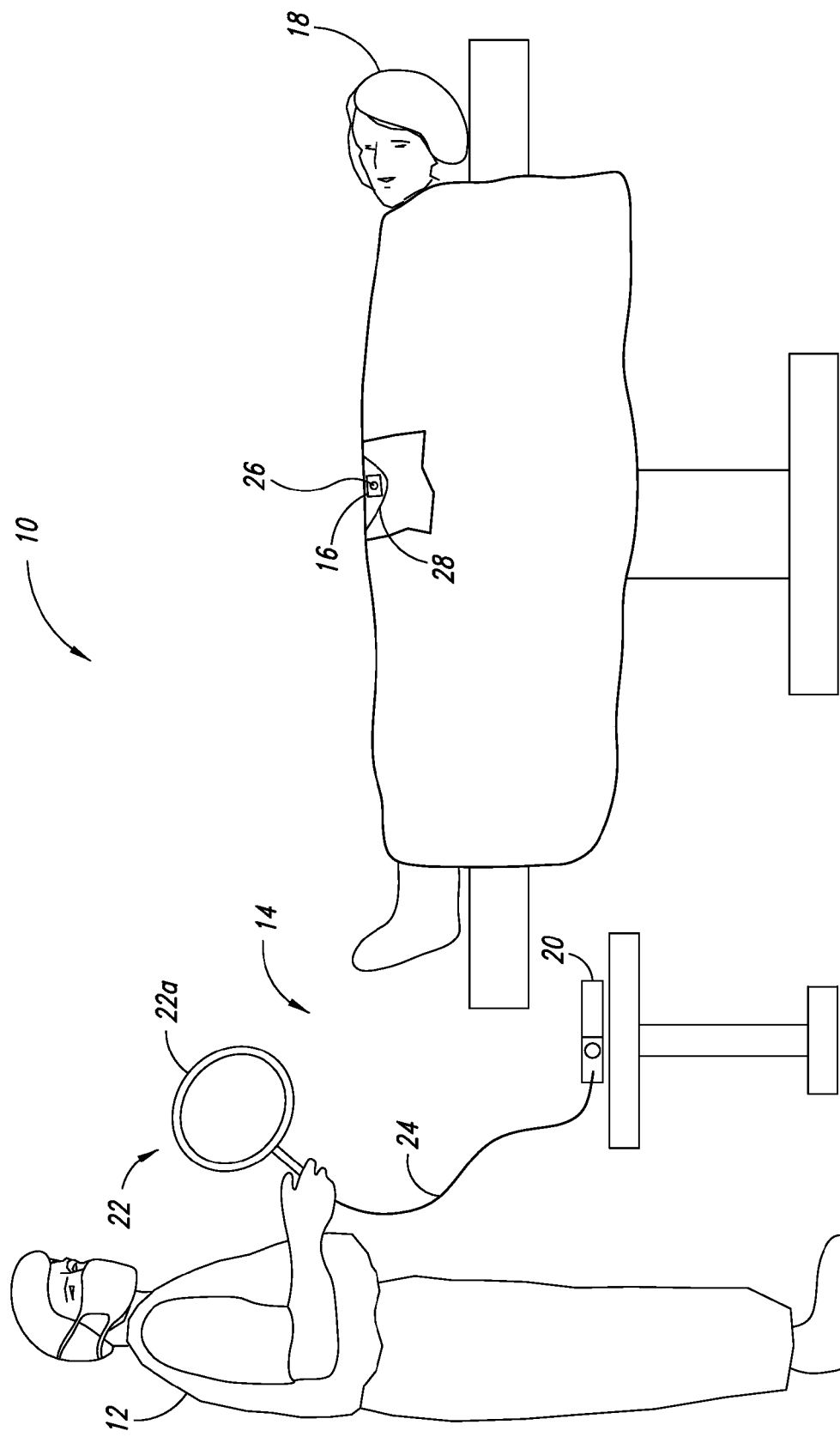

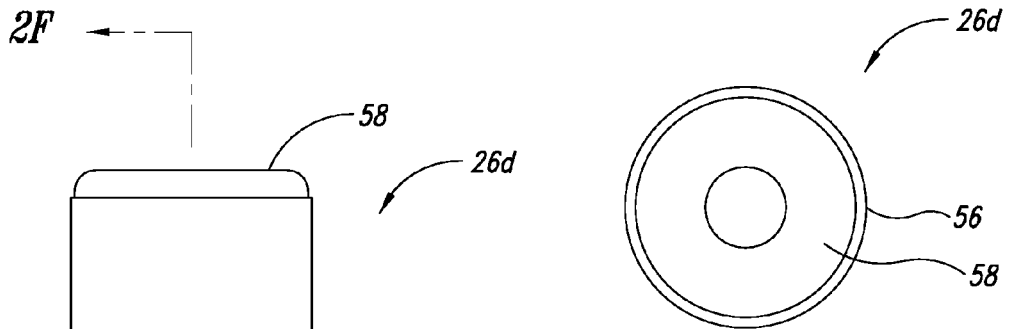
FIG. 2E
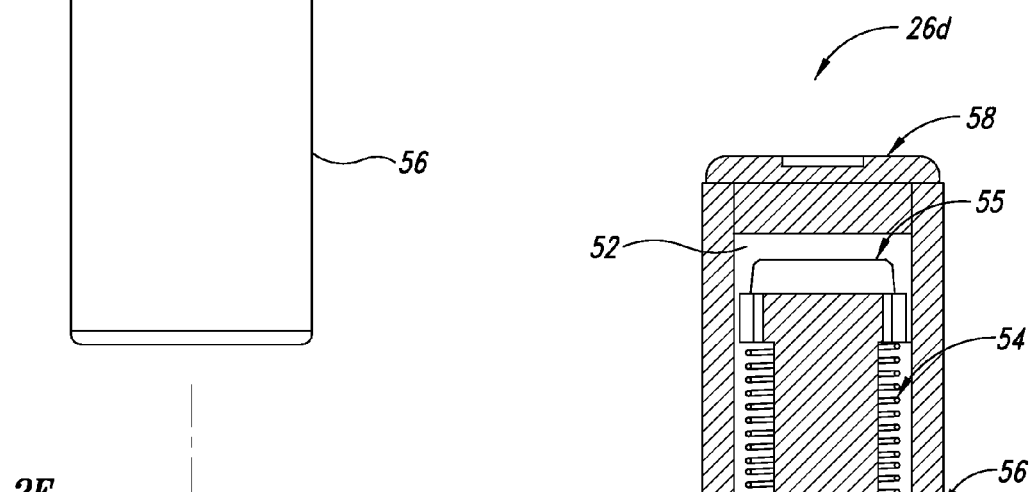
FIG. 2D
FIG. 2F
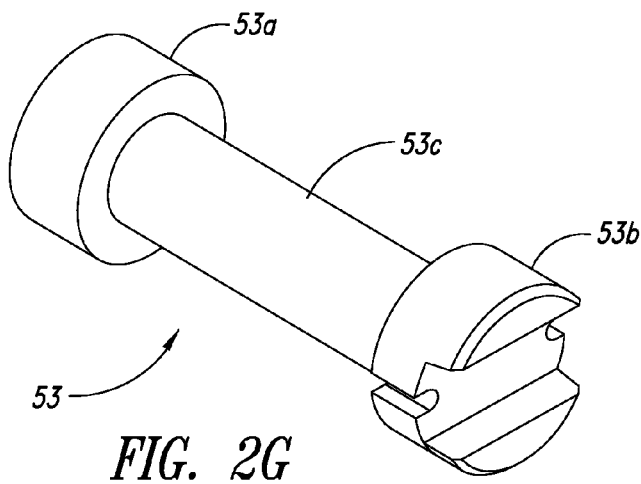
FIG. 2G

METHOD, APPARATUS AND ARTICLE FOR DETECTION OF TRANSPONDER TAGGED OBJECTS, FOR EXAMPLE DURING SURGERY

CROSS REFERENCE TO RELATED APPLICATIONS

This application claims benefit under 35 U.S.C. 119(e) to U.S. provisional patent application Ser. No. 60/892,208, filed Feb. 28, 2007, which is incorporated herein by reference in its entirety.

BACKGROUND

1. Field

This disclosure generally relates to the detection of the presence or absence of objects tagged with transponders, which may, for example, allow the detection of surgical objects during surgery.

2. Description of the Related Art

It is often useful or important to be able to determine the presence or absence of an object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Some facilities may wish to install a single interrogation and detection system in each surgery theater, while other facilities may move an interrogation and detection system between multiple surgical theaters. In either case, the overall system will require a large number of transponders, since at least one transponder is carried, attached or otherwise coupled to each object which may or will be used in surgery. Consequently, the transponders must be inexpensive. However, inexpensive transponders typically have a relatively large variation in the frequency of signals they emit, making it difficult to accurately detect the signals returned by the transponders. Consequently, a new approach to detection of the presence and absence of transponder that facilitates the use of inexpensive transponders is highly desirable.

BRIEF SUMMARY OF THE INVENTION

In one aspect, a method of operating a transponder detection device may be summarized as including automatically determining a first adjustment to spread energy across a first frequency band; automatically determining a second adjustment to spread energy across a second frequency band; transmitting a signal in the first frequency band during a first time; transmitting a signal in the second frequency band during a second time; receiving a response, if any, to the transmission of the signal in the first frequency band; and receiving a response, if any, to the transmission of the signal in the second frequency band.

In another aspect, a transponder detection device may be summarized as including adjustment determination means for automatically determining at least a first adjustment to spread energy across a first frequency band centered around a first center frequency and a second adjustment to spread energy across a second frequency band centered around a second center frequency; transmitting means for transmitting signals in at least the first frequency band during a first time and in the second frequency band during a second time; and adjusting means for adjusting the spread of energy in response to the adjustment determination means; receiving means for receiving a response, if any, from transponders, if any, to the transmissions of the signals in at least the first and the second frequency bands.

In yet another aspect, a transponder detection device may be summarized as including a transmitter circuit configured to produce signals in a plurality of frequency bands; a dynamic tuning circuit coupled to the transmitter circuit and configured to tune about a respective center channel within each of the frequency bands to increase an equalization of a distribution of energy in the respective frequency band; and a receiver circuit configured to receive signals returned by a transponder in response to the signals in the plurality of frequency bands.

In an even further aspect, a method of operating a transponder detection device may be summarized as including obtaining a backward looking noise sample during a first time; transmitting an interrogation signal in a first frequency band during a second time; obtaining a signal sample at a second time sufficiently close in time to the interrogation signal such that the obtained signal sample represents a return signal, if any, returned in response to the interrogation signal; obtaining a forward looking noise sample during a third time sufficiently spaced in time from the transmitting of the interrogation signal such that the forward looking sample does not represent the return signal, if any, returned in response to the interrogation signal; and comparing the signal sample to a greater of the forward and the backward looking noise samples to determine whether the signal sample contains the return signal.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 1 is a schematic diagram showing a surgical environment illustrating a medical provider using an interrogation and detection system to detect an object tagged with a transponder in a patient, according to one illustrated embodiment.

FIG. 2D is a side elevational view of a transponder, according to yet a further illustrated embodiment.

FIG. 2E is an end view of the transponder of FIG. 2D.

FIG. 2F is a cross-sectional view of the transponder of FIG. 2D, taken along section line 2F.

FIG. 2G is an isometric view of a ferrite core of the transponder of FIG. 2D.

DETAILED DESCRIPTION

Figure 2A:
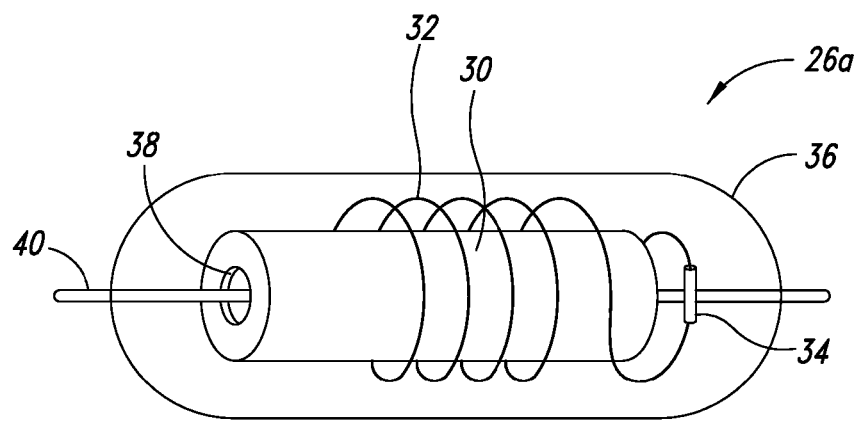
FIG. 2A is a schematic diagram of a transponder, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

FIG. 1 shows a surgical environment 10 in which a medical provider 12 operates an interrogation and detection system 14 to ascertain the presence or absence of objects 16 in, or on, a patient 18. The interrogation and detection system 14 may include a controller 20, and an antenna 22 coupled to the controller 20 by one or more communication paths, for example coaxial cable 24. The antenna 22 may take the form of a hand-held wand 22a.

The object 16 may take a variety of forms, for example instruments, accessories and/or disposable objects useful in performing surgical procedures. For instance, the object 16 may take the form of scalpels, scissors, forceps, hemostats, and/or clamps. Also for example, the objects 16 may take the form of surgical sponges, gauze and/or padding. The object 16 is tagged, carrying, attached or otherwise coupled to a transponder 26. Embodiments of the interrogation and detection system 14 disclosed herein are particularly suited to operate with transponders 26 which are not accurately tuned to a chosen or selected resonant frequency. Consequently, the transponders 26 due not require high manufacturing tolerances or expensive materials, and thus may be inexpensive to manufacture.

In use, the medical provider 12 may position the wand 22a proximate the patient 18 in order to detect the presence or absence of the transponder 26, and hence an object 16. The medical provider 12 may in some embodiments move the wand 22a along and/or across the body of the patient 18. In some embodiments, the wand 22a may be sized to fit at least partially in a body cavity 28 of the patient 18.

FIG. 2A shows a transponder 26a according to one illustrated embodiment.

The transponder 26a includes a miniature ferrite rod 30 with a conductive coil 32 wrapped about an exterior surface thereof to form an inductor (L), and a capacitor (C) 34 coupled to the conductive coil 32 to form a series LC circuit. The conductive coil 32 may, for example, take the form of a spiral wound conductive wire with an electrically insulative sheath or sleeve. The transponder 26a may include an encapsulation 36 that encapsulates the ferrite rod 30, conductive coil 32, and capacitor 34. The encapsulant 36 may be a bioinert plastic, that protects the ferrite rod 30, conductive coil 32 and/or capacitor 34 from pressure and/or from fluids, for example bodily fluids.

In some embodiments, the ferrite rod 30 may include a passage 38 sized to receive a physical coupler, for example a bonding tie or string 40. The bonding tie or string 40 may take the form of an elastomeric x-ray opaque flexible elongated member, that may be used to attach the transponder 26a to various types of objects 16, for example surgical sponges. The transponder 26a may have a length of about 8 millimeters and a diameter of about 2 millimeters. Employing such small dimensions ensures that the transponder 26a does not impede deformation of objects 16 such as sponges. The transponder 26a may include an optional diode (not shown), to protect against over-voltage occurrences caused by other electronic instruments.

Figure 2B:
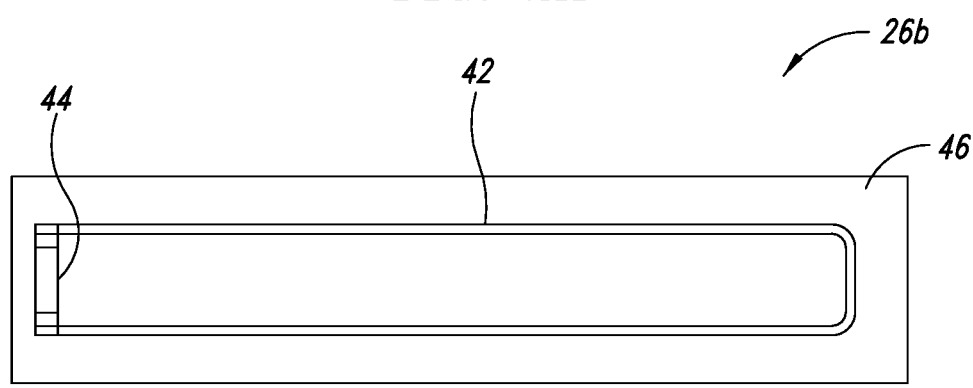
FIG. 2B is a schematic diagram of a transponder, according to another illustrated embodiment.

FIG. 2B shows a transponder 26b, according to another illustrated embodiment.

The transponder 26b includes a single loop of conductive material 42, for example a loop of conductive wire forming an inductor (L), coupled in series to a capacitor 44 (C) to form an LC series circuit. The loop of conductive material 42 and capacitor 44 may be encapsulated in an elastomeric coating or sleeve 46. The dimensions of the transponder 26b may be similar to the dimensions of the transponder 26a. In some embodiments, the dimensions of the transponder 26b are greater than the dimensions of the transponder 26a. The transponder 26b is highly flexible, and thus may provide its own thread-like or string-like attachment to various types of objects 16.

Figure 2C:
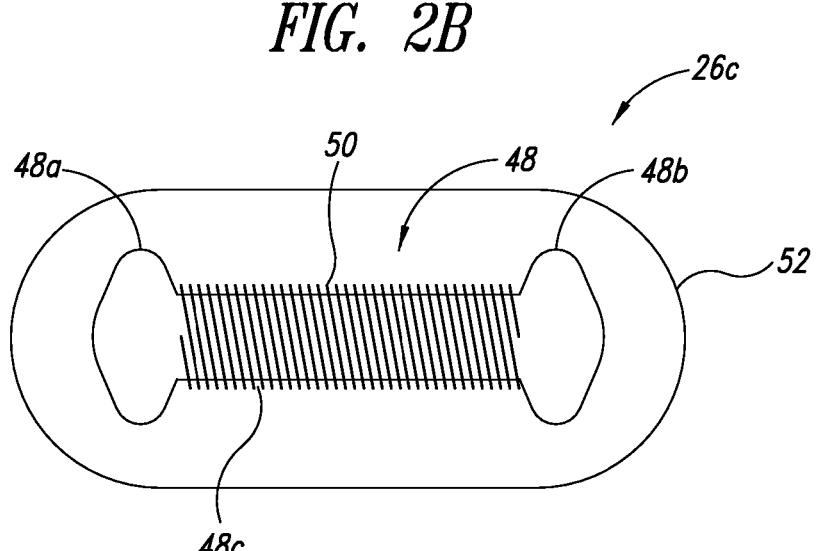
FIG. 2C is a schematic diagram of a transponder, according to a further illustrated embodiment.

FIG. 2C shows a transponder 26c according to a further embodiment.

The transponder 26c includes a dumbbell-shaped ferrite rod 48 having broad end portions 48a, 48b, and a narrow intermediate portion 48c which is wrapped by a conductive coil 50. The broad portions 48a, 48b contain the conductive coils 50. Such a design may provide stronger and/or more reliable signal emission than transponders 26a, 26b fashioned with cylindrical ferrite rods. The transponder 26c may optionally include an encapsulant 52. Further details regarding the transponder 26c may be found in U.S. Provisional Patent Application No. 60/811,376 filed Jun. 6, 2006. In some embodiments, the transponder 26c may be formed as a fusiform-shaped object, with truncated ends. The fusiform shape may be advantageous over cylindrical shaped transponders 26a, 26b in reducing the likelihood of close parallel alignment of the transponders 26a, 26b, which may produce transponder-to-transponder interaction and interference.

FIGS. 2D-2G show a transponder 26d according to yet a further embodiment.

The transponder 26d includes a ferrite core 53, inductor (L) 54, and capacitor© 55 electrically coupled to the inductor 54 to form an LC series circuit. The transponder 26d also includes a capsule 56 with a cavity 57 open at one end to receive the ferrite core 53, inductor 54 and capacitor 55, as well as a lid 58 to close the open end of the capsule 56.

The ferrite core 53 may, for example, take the form of a soft ferrite drum, and may, for example, be formed of Nickel Zinc. Suitable ferrite cores 53 may be commercially available from TAK FERRITE as part no. L8A DR3X9 B=1.8 F=6 or from HUAH YOW under part no. 10R030090-77S. The drum may have a pair of larger diameter end portions 53a, 53b, with a smaller diameter intermediate portion 53c therebetween.

The inductor 54 may take the form of magnet wire wrapped around the intermediate portion 53c of the ferrite core 53. The magnet wire may, for example, have a dimension of approximately 41 American Wire Gauge (AWG), although some embodiments may employ wires or conductors of larger or small gauges. Suitable inductors 54 may be commercially available from ELEKTISOLA under part no. PN-155 or from ROSEN under part no. 2UEW-F. The inductor may, for example, include approximately 432 turns, over approximately 6.5 layers, although some embodiments may include a greater or lesser number of turns and/or layers. The transponder 26d may include tape and/or epoxy enveloping the inductor 54. Suitable tape may be commercially available from 3M under part nos. 1298, 1350-1 or PLEO 1P801, while suitable epoxy may be commercially available from LOCKTITE under part no. 3211.

The capacitor 55 may, for example, take the form of a ceramic capacitor. The capacitor 55 may, for example, have a capacitance of 470PF, 100V, with a Quality factor of Q>2200@1 MHz. Suitable capacitors 55 may be commercially available from SANJV DIELECTRIC under part no. 0805NPO471J101 or from FENG HUA under part no. 0805CG471J101NT.

The capsule 56 and lid 58 may, for example, be formed of a polypropylene. Suitable capsules 56 and lids 58 may be commercially available from WEITHE ELECTRON (HK) COMPANY, under part specification CASE 4.3×12.6. The combination of the capsule 56 and lid 58 may, for example, have a length of approximately 12.8 mm and a diameter of 4.4 mm. Circuit bonds may, for example, employ UNITED RESINS CORP. part no. 63001500 CIRCUIT BOND LV, while solder may take the form of a lead free 96.5% Ag/3% Sn/0.5Cu solder.

The transponders 26 may be attached to hemostats, scissors, certain forms of forceps, and the like. In some embodiments, the transponders 26 may be coupled to the object 16 by way of a clamp or holder. In some embodiments, the transponders 26 may be retained within a cavity of the holder. In some embodiments, the holder may be fashioned of a durable deformable material, such as surgical grade polymer, which may be deformed to clamp securely onto the finger or thumbhole of an instrument. In other embodiments, the transponders 26 may be attached to objects 16 by way of pouches fashioned of sheet material (e.g., surgical fabric) surrounding the transponder 26. The transponder 26 is retained within the pouch, and in some embodiments the pouch may be sewn or otherwise sealed. Sealing may be done with adhesive, hot glue, clamping, grommeting, or the like.

Figure 3A:
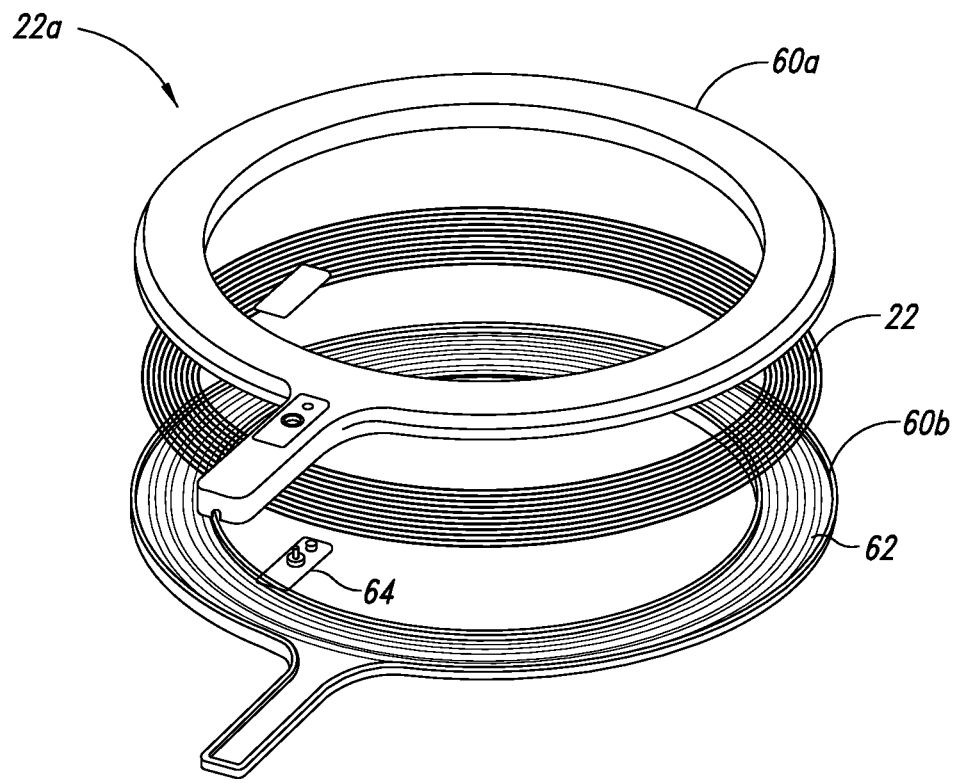
FIG. 3A is an exploded view of a wand of the interrogation and detection system, according to one illustrated embodiment.
Figure 3B:
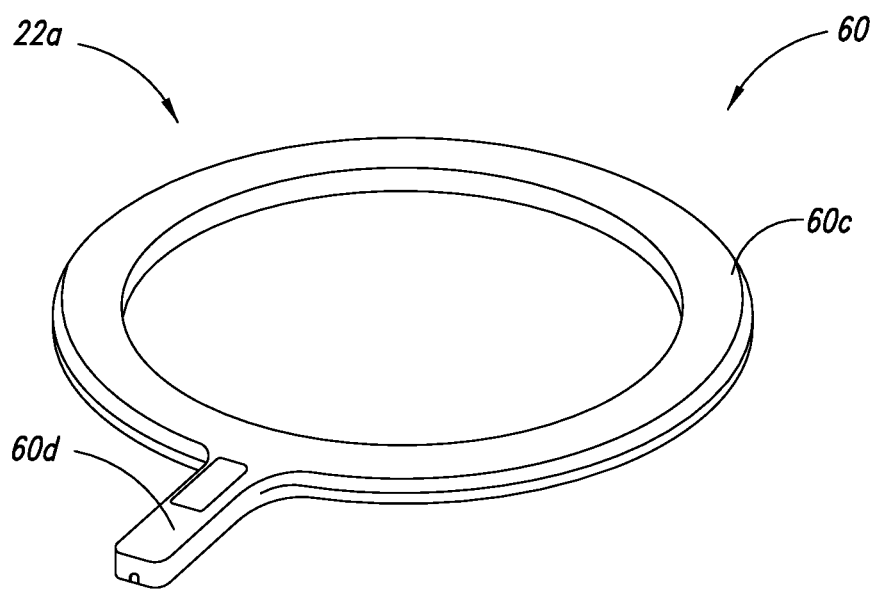
FIG. 3B is an isometric view of the wand of FIG. 3A.

FIGS. 3A and 3B show a wand 22a, according to one illustrated embodiment.

The wand 22a may include a first housing structure 60a and a second housing structure 60b which mates to the first housing structure 60a to form a housing 60. The housing 60 may include an annular portion 60c and a handle portion 60d extending from the annular portion. The handle portion may be sized and dimensioned to be gripped by the hand of a medical provider 12 (FIG. 1). In some embodiments, the housing portions 60a, 60b may be identical in shape to one another.

The housing 60 may define one or more cavities 62 sized and dimensioned to receive the antenna 22. The antenna 22 may, for example, take the form of an annulus or air-coil formed of coils of conductive material, for example wire. In one embodiment, the antenna 22 includes 10 turns evenly spaced between an inner diameter of about 11 inches and an outer diameter of about 14 inches. The antenna 22 acts as an inductor.

The wand 22a may include a coupling member 64 which may be positioned in the cavity in the handle portion 60d to provide a connector to communicatively couple to an end of the coaxial cable 24 to the antenna 22. The coupling member 64 may take the form of a standard coaxial connector. Some embodiments may employ other types of communications pathways between the controller 20 and the antenna 22, and thus may employ other types of coupling members or connectors.

In some embodiments, the wand 22a may include one or more user interface devices, for example one or more visual indicators to provide visual indications to the medical provider 12. Such may, for example, take the form of one or more light emitting diodes, which may produce one or more different colors. Such user interface devices may additionally, or alternatively include a speaker or other transducer, operable to produce a sound or other sensory indication, for example a tactile sensation. Such user interface devices may be configured to provide sensory feedback to the medical provider 12 indicative of an operating condition of the interrogation and detection system 14. For example, such may indicate when the interrogation and detection system 14 is operating, when the presence of a transponder 26 has been identified, and/or when an error has occurred. Locating user interface devices on the wand 22a may be advantageous since the medical provider 12 will typically focus their attention on the wand 22a while scanning the patient 18.

Figure 4:
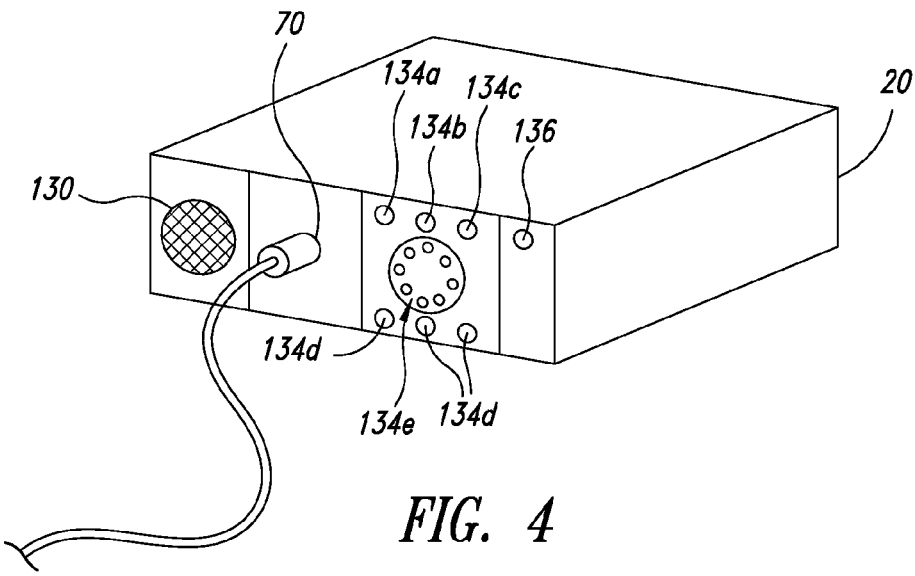
FIG. 4 is an isometric view of a controller of the interrogation and detection system, according to one illustrated embodiment.

FIG. 4 shows the controller 20 according to one illustrated embodiment.

The controller 20 includes an input port 70 with an appropriate coupling member, for example a connector to allow an end of the coaxial cable 24 to be communicatively coupled to the controller 20. As noted above, some embodiments may employ other communications pathways between the controller 20 and the antenna 22, hence other types of coupling members or connectors may be employed. The controller 20 may also include a power switch (not illustrated in FIG. 4), for example, positioned on a back or rear of the controller 20. The controller 20 may further include a power cord (not shown) to couple the controller 20 to a suitable power supply. The power supply may, for example take the form of a standard wall outlet or any other power supply or source. The controller 20 may further include one or more user interface devices for providing information to a user. For example, the controller 20 may include one or more visual indicators 134, for instance one or more light emitting diodes (LEDs) and/or liquid crystal displays. Additionally, or alternatively, the controller 20 may include one or more speakers 130 or other transducers operable to produce sound or tactile sensations.

Figure 5:
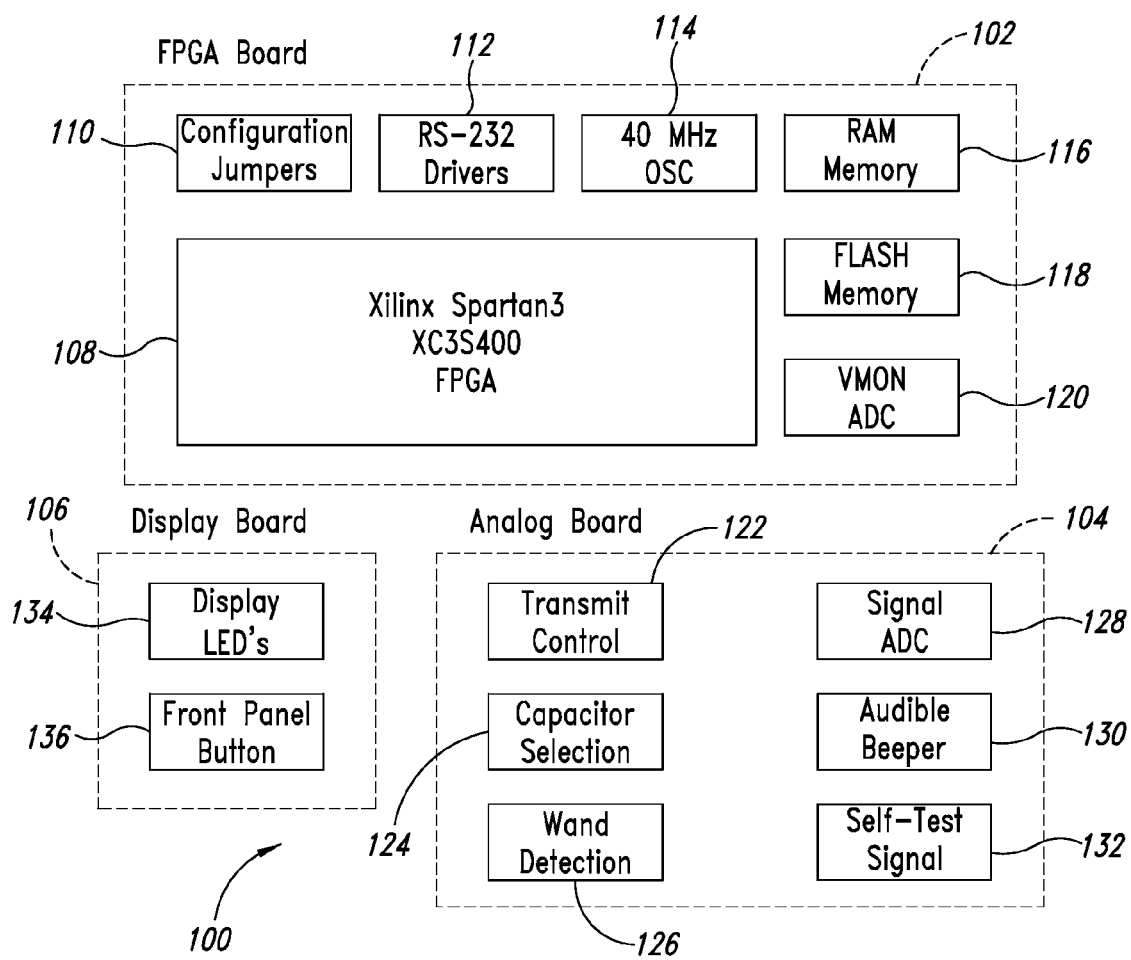
FIG. 5 is a schematic diagram of a control system of the interrogation and detection system, according to one illustrated embodiment.

FIG. 5 shows a control system 100 of the interrogation and detection system 14, according to one illustrated embodiment.

The control system 100 includes a field programmable gate array (FPGA) board 102, analog board 104 and display board 106, communicatively coupled to one another.

The FPGA board includes an FPGA 108, configuration jumpers 110, RS-232 drivers 112, oscillator 114, random access memory (RAM) 116, flash memory 118, and voltage monitoring (VMON) analog-to-digital converter (ADC) 120.

The FPGA 108 may take the form of a Xilinx Spartan3 FPGA, which runs FPGA and application software. As explained below, on power up, the FPGA reads the configuration information and application software program from the flash memory 118.

The configuration jumpers 110 are used to select the application software configuration.

The RS-232 drivers 112 are used to allow the application software to communicate using serial RS-232 data for factory test and diagnostics.

The oscillator 114 sets the clock frequency for the operation of the FPGA 108. The oscillator 114 may, for example, take the form of 40 MHz oscillator, although other frequencies are possible.

The RAM 116 is connected to the FPGA 108 and is available for use by the application software. The application software uses this memory space for storage of both the executable program and program data. The RAM 116 may, for example, have a capacity of 1 MB.

The flash memory 118 contains both the FPGA configuration data and the binary application program. On power up the FPGA 108 reads the flash memory to configure the FPGA 108 and to copy the application program binary data from the flash memory 118 to the RAM 102.

The voltage monitor ADC 120 is connected to the FPGA 108 and controlled by the application software to monitor a power supply and regulated voltage forms in controller electronics.

The analog board 104 includes transmit control circuits 122, capacitor selection circuits 124, wand detection circuit 126, signal ADC 128, audible beeper 130 and self-test signal 132.

Figure 7A:
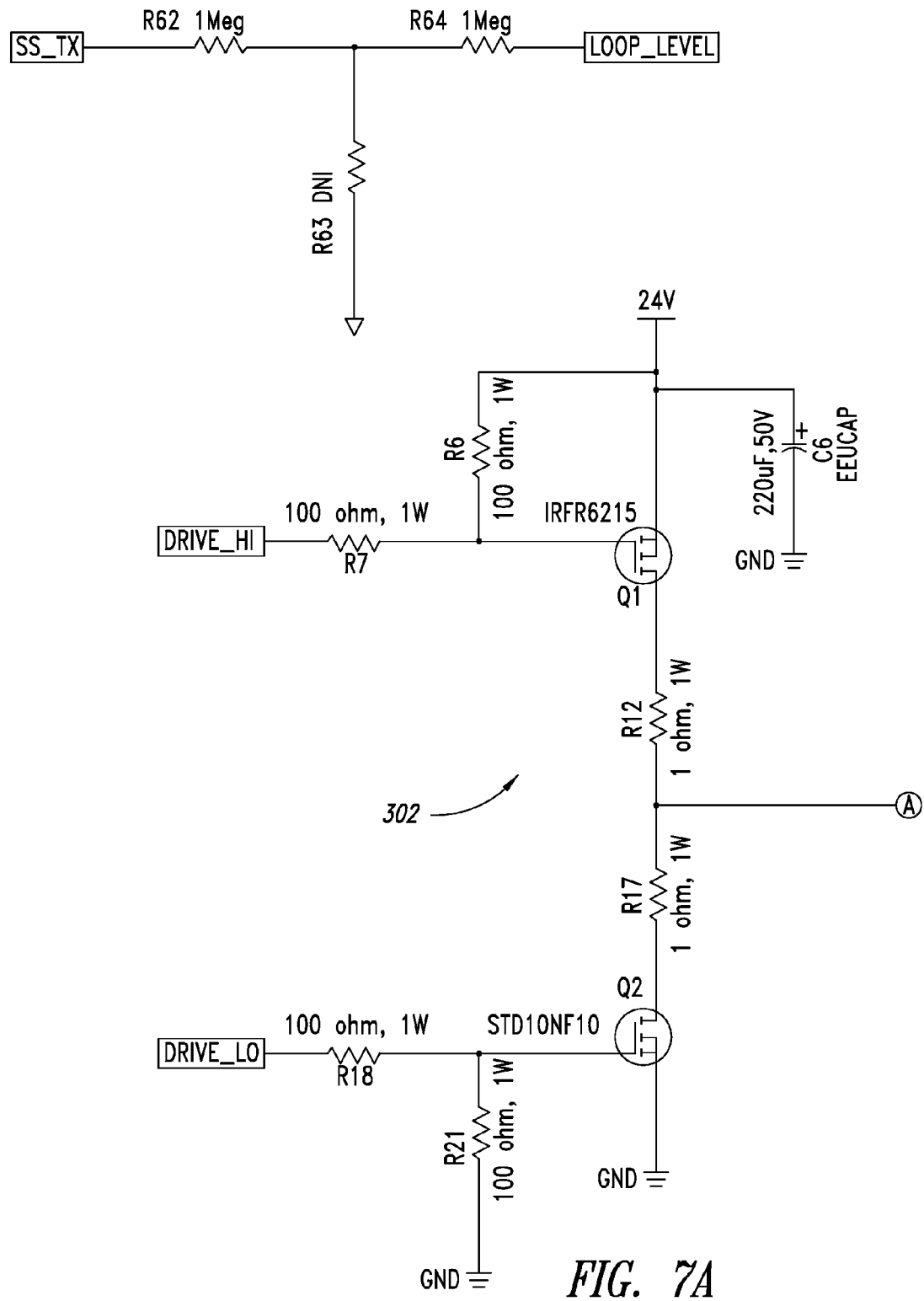
FIGS. 7A-7I are an electrical schematic diagram of the interrogation and detection system including a control circuit and antenna, according to one illustrated embodiment.
Figure 7B:
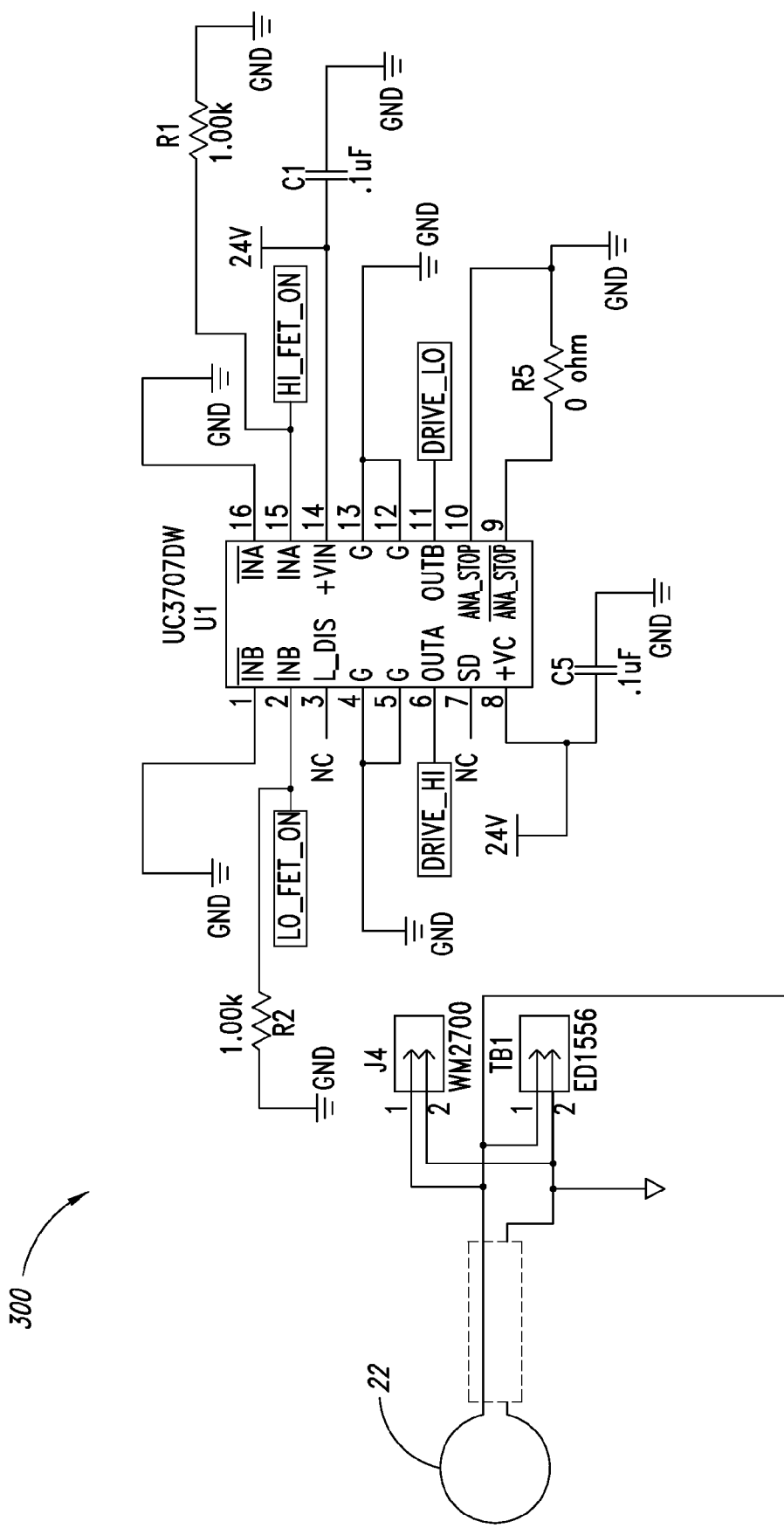
Figure 7C:
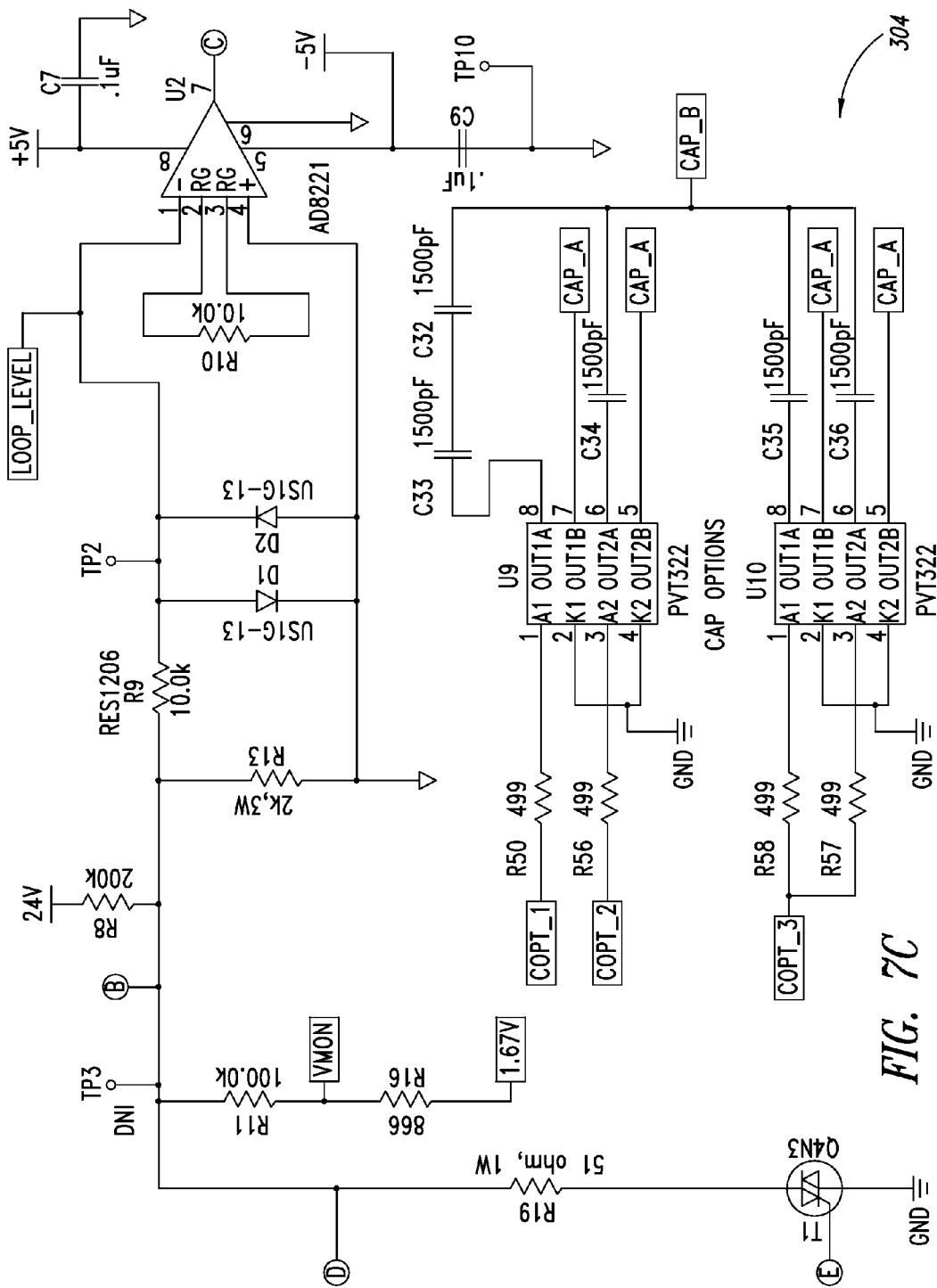
Figure 7D:
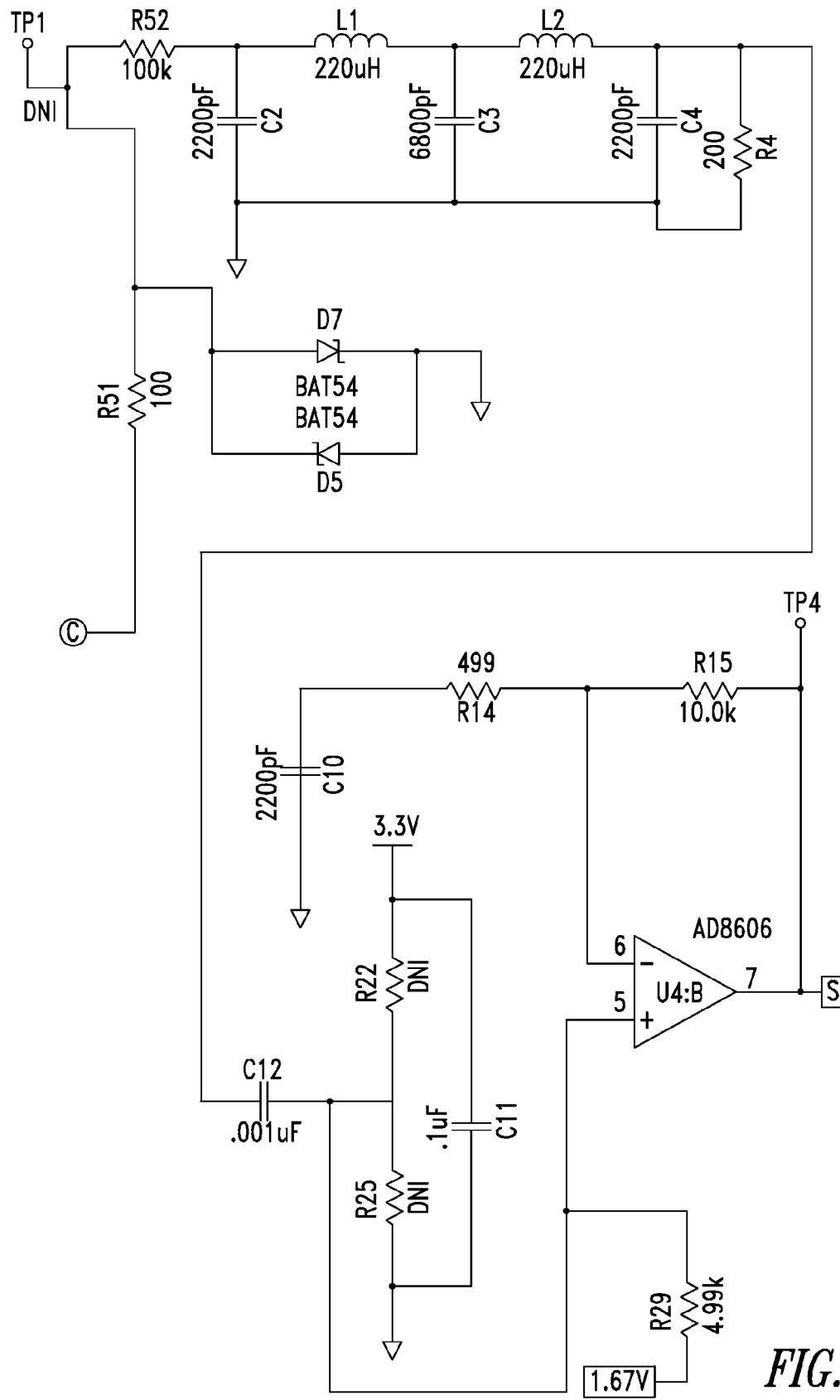
Figure 7E:
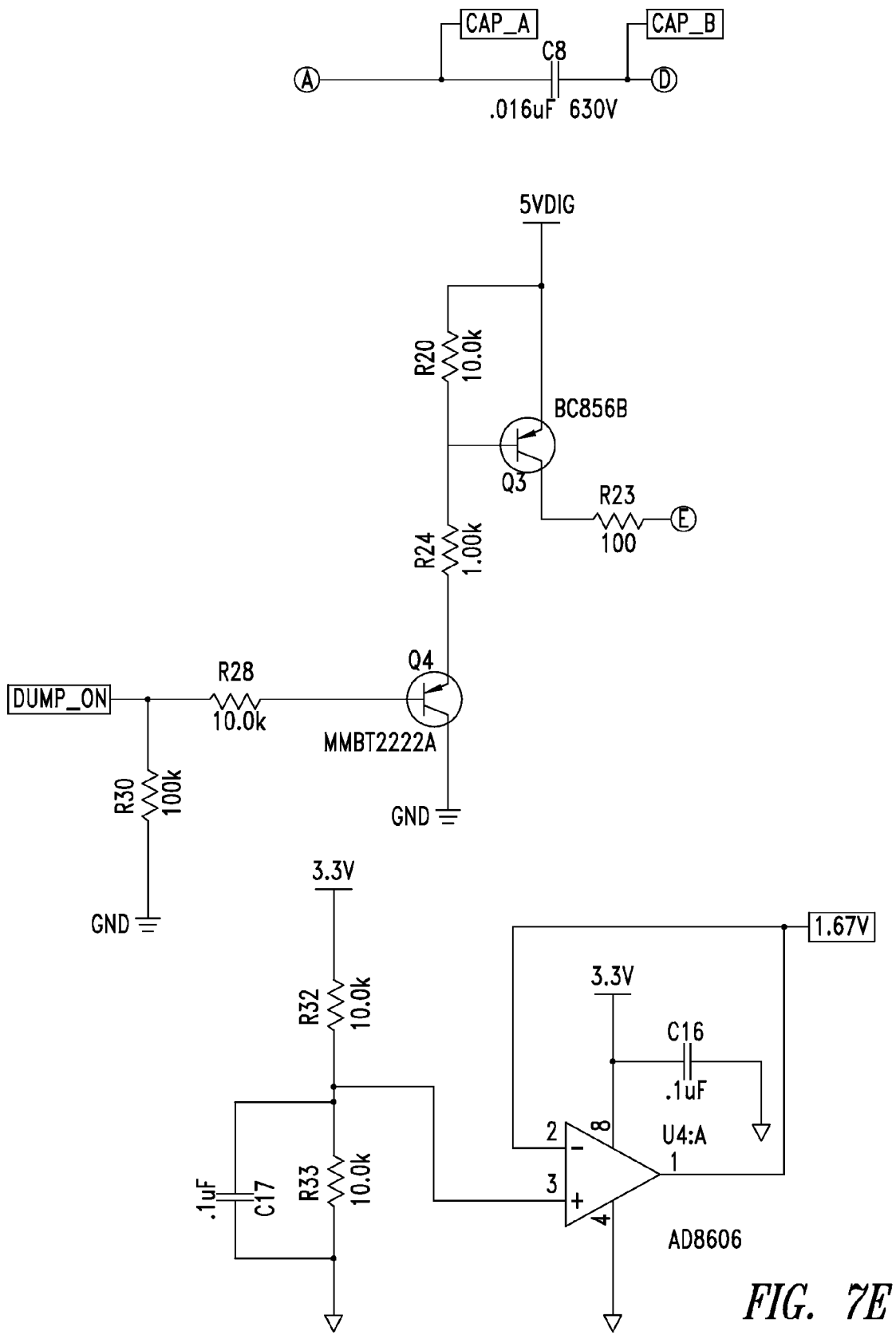
Figure 7F:
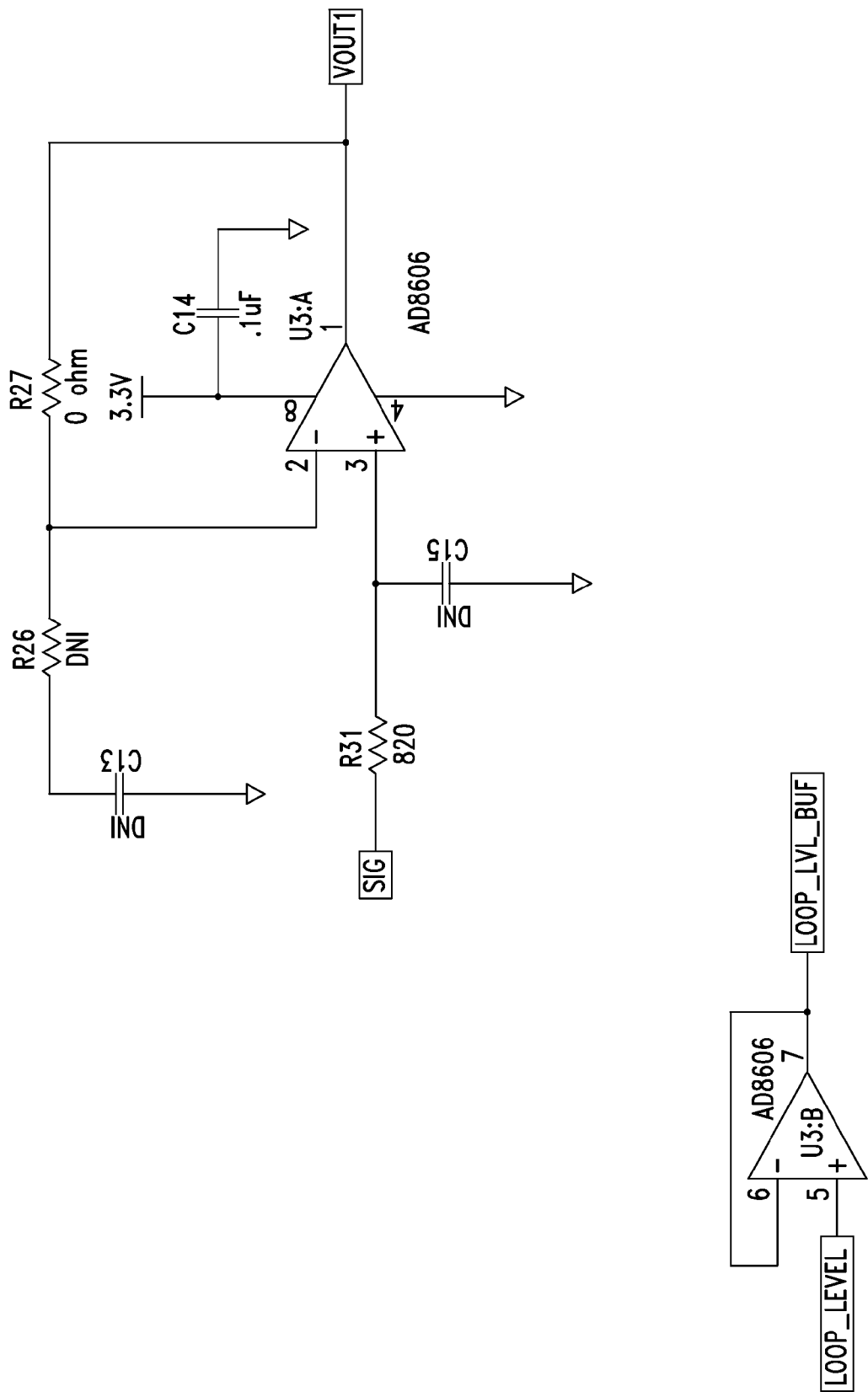
Figure 7G:
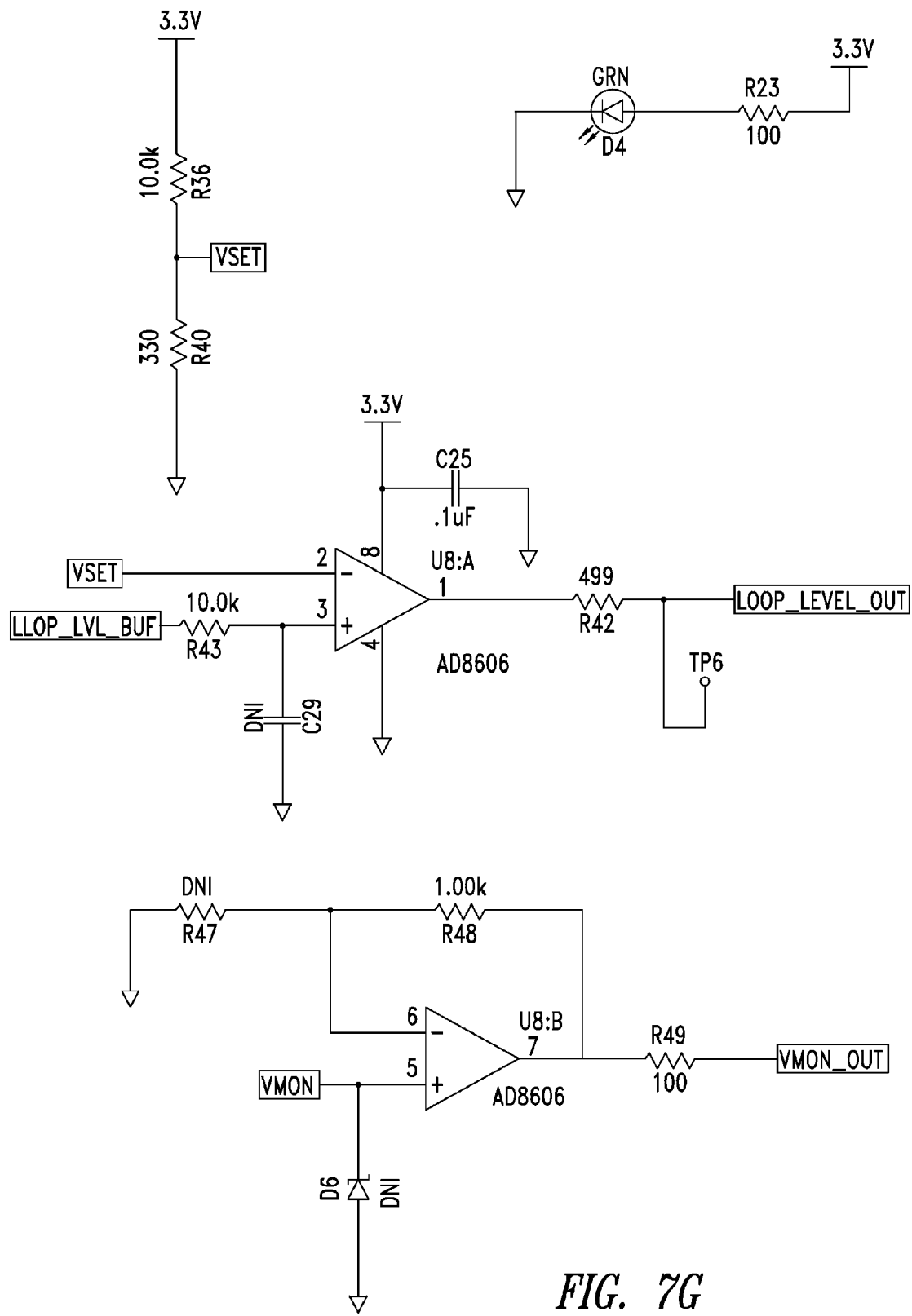
Figure 7H:
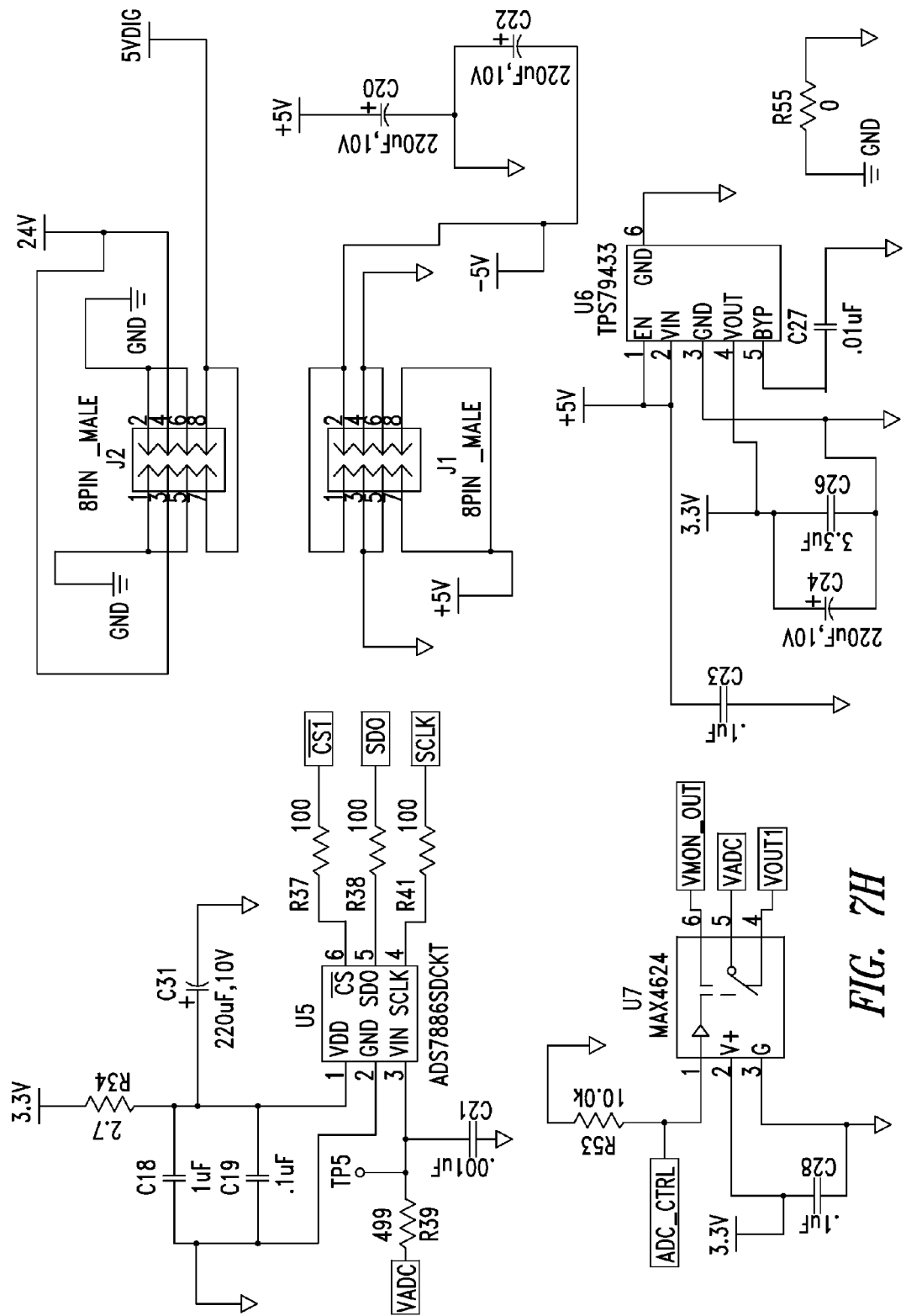
Figure 7I:
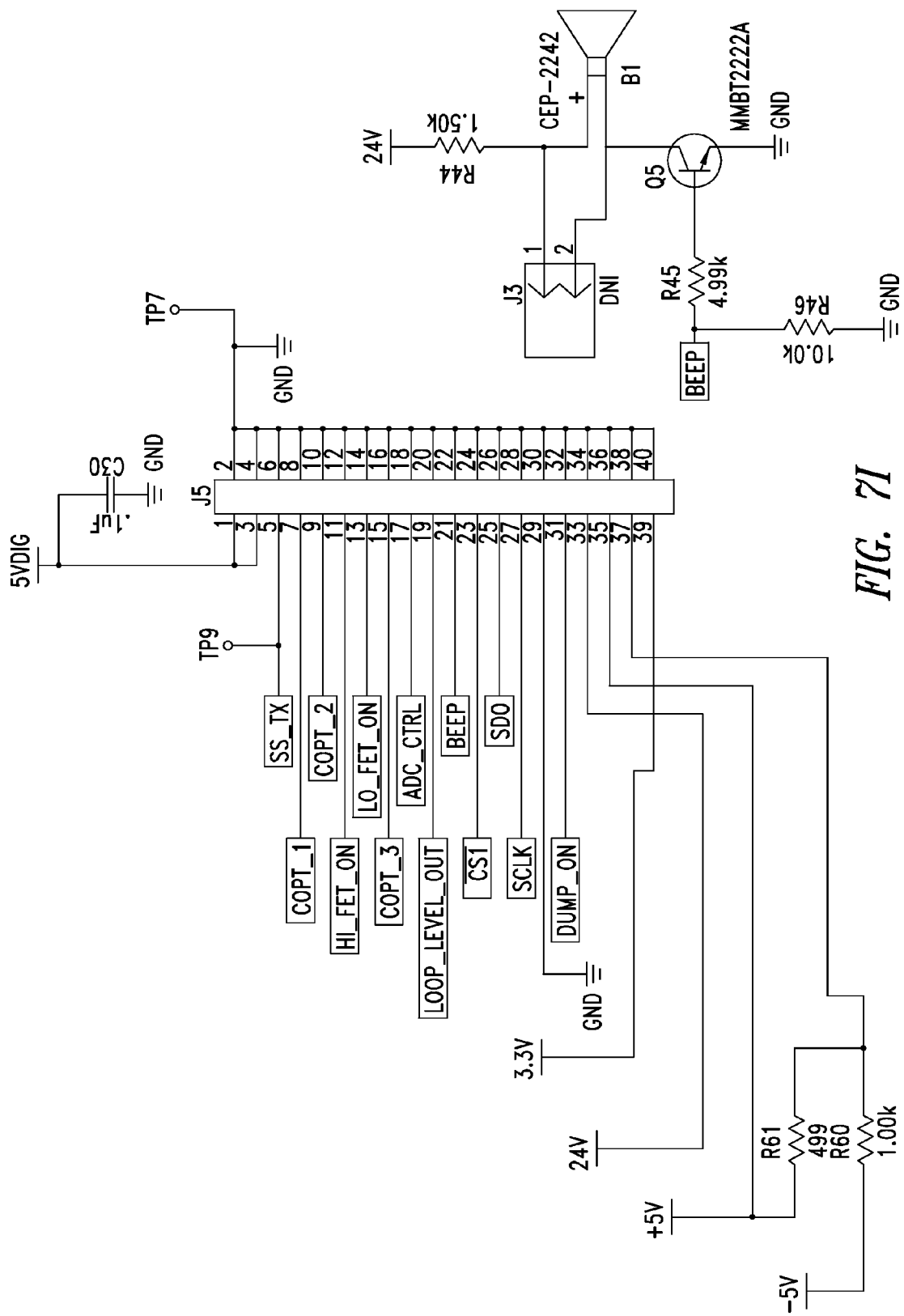

The transmit control circuits 122 on the analog board 104 are controlled by signals from the FPGA 108 to generate a transmit waveform. These signals are denominated as LO_FET_ON and HI_FET_ON, which control the transmit or drive transistors Q1, Q2 (FIG. 7A) along with a signal denominated as DUMP_ON which controls a dump TRIAC (FIG. 7A).

The capacitor selection circuits 124 on the analog board 104 are controlled by the signals from the FPGA 108 to tune the drive circuit to match an inductance of the antenna 22.

The wand detection circuit 126 detects when a wand 22a is connected to the controller 20. The output of the wand detection circuit 126 drives a signal denominated as the LOOP_LEVEL_OUT signal, which is an input to the FPGA 108.

The signal ADC 128 is used to sample the signals received at the antenna 22a from the transponders 26 (FIGS. 2A-2C). The signal ADC 128 may, for example, operate at a 1 MHz sample rate and may have 12-bits of resolution. The FPGA board 102 generates the timing and control signals for the signal ADC 128, which signal are denominated as ADC_CTRL, CS1, SCLK, SD0.

The audible speaker or beeper 130 can be controlled by the FPGA 108 to emit sounds to indicate various states, modes or operating conditions to the medical provider 12 (FIG. 1).

The FPGA 108 can cause the generation of the self test signal 132 on the analog board 104 at the signal ADC 128. Self-testing may be performed at start up, and/or at other times, for example periodically or in response to the occurrence of certain conditions or exceptions.

The display board 106 includes user interface elements, for example a number of light emitting diodes (LEDs) 134. The FPGA board 102 can control the LEDs 134 on the display board 106. The display board 106 also includes a user selectable activation switch, denominated as front panel button 136. The front panel button 136 is connected to the display board 106 which allow the FPGA 108 to monitor when the front panel button 136 is activated (e.g., pressed).

Figure 6:
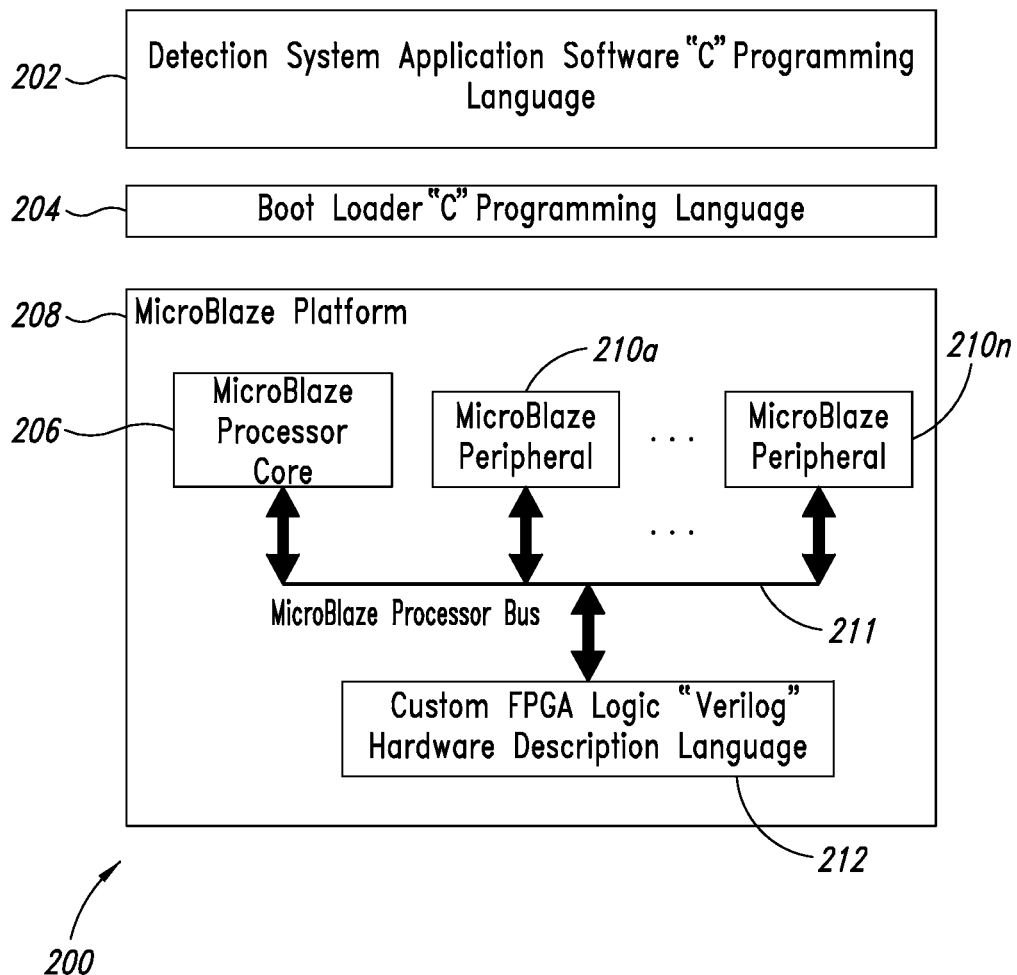
FIG. 6 is a schematic diagram of a software configuration of the interrogation and detection system, according to one illustrated embodiment.

FIG. 6 shows a software configuration 200 of the interrogation and detection system 14, according to one illustrated embodiment.

The software may include application software 202 that is responsible for operating the electronics controller 20 (FIGS. 1 and 4). The application software 202 controls the timing for generating transmit pulses, processes sampled data to detect transponders 26 (FIGS. 2A-2C), and indicates status to the user with the display LED's 134 (FIG. 5) on the display board 106 and/or via the audible speaker or beeper 130 on the analog board 104. The application software 202 is stored in the flash memory 118 (FIG. 5) and transferred into the RAM 116 by a boot loader 204.

The boot loader 204 is automatically loaded when the FPGA 108 is configured, and starts execution after a processor core 206 is reset. The boot loader 204 is responsible for transferring the application software 202 from the flash memory 118 to the external RAM 116.

The processor platform 208 is configured into the FPGA 108 (FIG. 5) on power up from the configuration information stored in the flash memory 118. The processor platform 208 implements a custom microprocessor with a processor core 206, peripherals 210a-210n, and custom logic 212.

The processor core 206 may take the form of a soft processor core supplied by XILINX under the name MICROBLAZE, that implements a 32-bit processor including memory cashes and a floating point unit. A soft core processor is one that is implemented by interconnected FPGA logic cells instead of by a traditional processor logic. The processor core 206 is connected to the internal FPGA peripherals 210a-210n using a 32-bit processor bus 211 called the On-Chip Peripheral Bus. The XILINX supplied peripherals for the MICROBLAZE processor core 206 include external memory interfaces, timers, and general purpose I/O.

The custom logic 212 to create the transmit signals, sample the ADC, and accumulate the transponder return signals is designed as a peripheral to the processor core 206. The custom logic 212 is the part of the design of the FPGA 108.

FIGS. 7A-7I show a control circuit 300 according to one illustrated embodiment. The control circuit 300 is used to drive the antenna 22 to excite or interrogate transponders 26 (FIGS. 2A-2C), and to detect and process signals received by the antenna 22 from the transponders 26.

The control circuit 300 includes a transmitter circuit 302 formed by a pair of drive transistors (e.g., field effect transistors) Q1, Q2 operated in a push-pull configuration between a high voltage rail (e.g., 24 V) and a low voltage rail (e.g., GND). The drive transistors Q1, Q2 are responsive to respective drive signals DRIVE_HI, DRIVE_LO, which are applied to the gates of the respective drive transistors Q1, Q2. The drive transistors Q1, Q2 are coupled to the antenna 22 by a non-switched capacitor C8 and the coaxial cable 24. The antenna 22 and capacitor C8, as well as capacitance provided by the coaxial cable 24, form an LC circuit.

The control circuit 300 also includes a dynamic tuning circuit 304. The dynamic tuning circuit 304 selectively adjusts the capacitance of the LC circuit. In the illustrated embodiment, the dynamic tuning circuit 304 includes a number of switched capacitors C33-C36 and relays U9, U10. The relays U9, U10 are operated to selectively couple the switched capacitors C33-C36 in series with the non-switched capacitor C8, thereby adjusting the LC characteristics of the LC circuit, and allowing fine tuning of the LC circuit around center frequencies or center channels of a number of wide band frequency bands, as described in more detail below.

Figure 8:
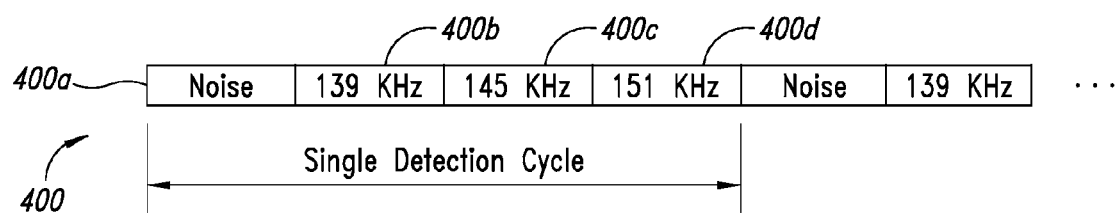
FIG. 8 is a timing diagram illustrating a method of frequency hopping, according to one illustrated embodiment.

FIG. 8 illustrates a detection cycle 400 that employs frequency hopping, according to one illustrated embodiment.

The application software 202 (FIG. 6) implements the detection cycle 400 using transmission or interrogation in frequency bands centered around at least two center channels or frequencies. In the illustrated embodiment, the application software 202 sequences through a pattern of four different measurements each detection cycle 400. During the first measurement 400a of each detection cycle, the transmitter is turned OFF to take a measurement of the ambient noise. The next three measurements 400b-400d are taken using different transmit frequency bands, for example around 139 KHz, 145 KHz and 151 KKHZ center channels or center frequencies of respective bands.

Figure 9:
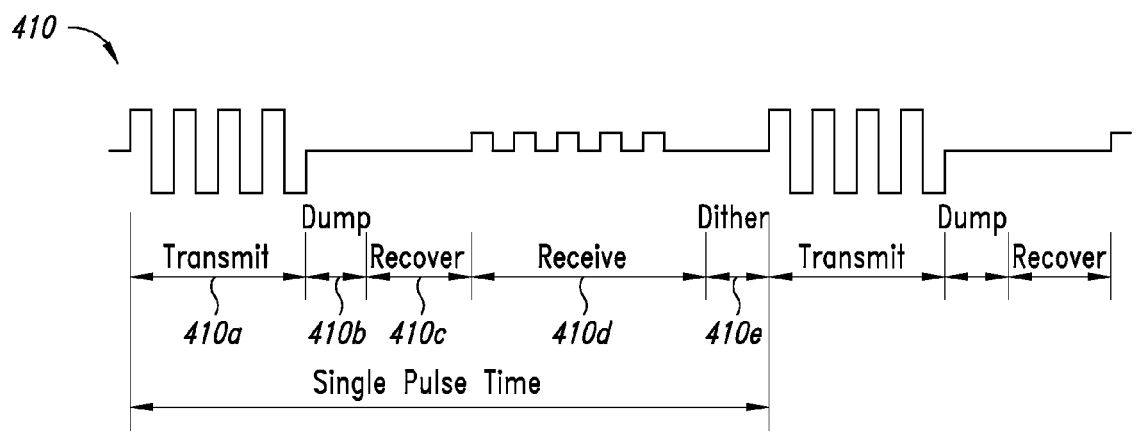
FIG. 9 is a timing diagram illustrating pulsed timing, according to one illustrated embodiment.

FIG. 9 illustrates pulse timing, according to one illustrated embodiment.

The custom logic in the FPGA 108 generates the timing and control signals for each pulse 410. During a transmit portion 410a of the pulse 410, the logic of the FPGA 108 drives the drive transistor control lines to generate the transmit signal. The FPGA logic controls the frequency of the transmit signal. During a dump portion 410b of the pulse 410, the logic of the FPGA 108 drives the gate of the dump TRIAC T1 to quickly drain the transmit energy from the antenna 22 in order to allow detection of the response signal form the transponder 26, if any. A recovery portion 410c of the pulse 410 allows receive filters and amplifiers to recover from the transmitted pulse before detecting the response signal from the transponder 26, if any. During the receive portion 410d of the pulse 410, the FPGA 108 controls the signal ADC 128 to sample the response signal from the transponder 26, if any. The signal ADC 128 may, for example, sample at a 1 MHz sample rate with a 12-bit resolution. A dither portion 410e of the pulse 410 has a random variable length of time, and may, for example be generated by a pseudo-noise (PN) sequence generator. Adding a random length of time between pulses de-correlates the response signal received from the transponder 26 from constant frequency sources of interference, if any.

Figure 10:
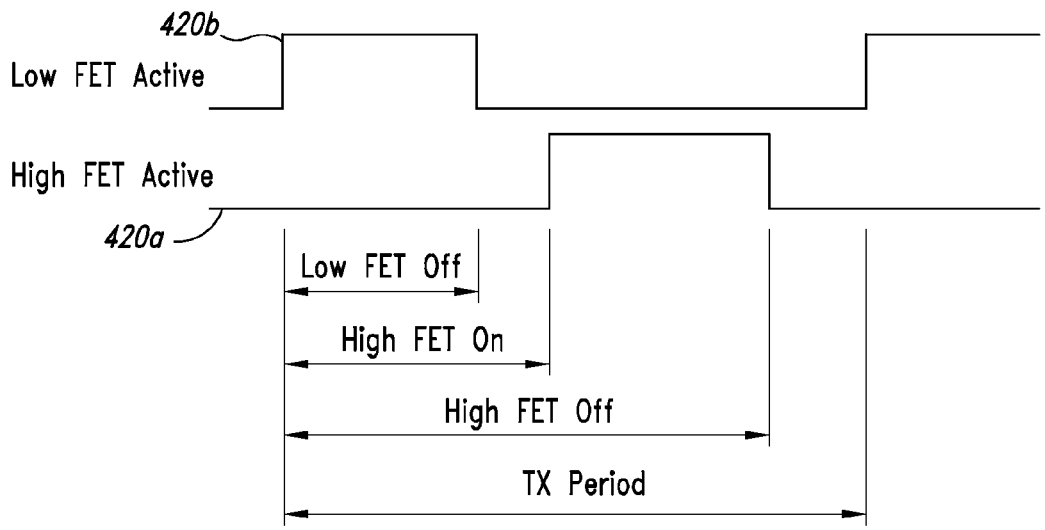
FIG. 10 is a timing diagram showing activation of a pair of transistors of the control circuit in a push-pull configuration to drive the antenna, according to one illustrated embodiment.

FIG. 10 shows signal timing for driving the drive transistors Q1, Q2 (FIG. 7A), according to one illustrated embodiment.

The custom logic in the FPGA 108 (FIG. 5) generates the signals 420a, 420b to drive the drive transistors Q1, Q2 (FIG. 7A) during the transmit portion 410a (FIG. 9) of the pulse 410. A transmit (TX) period value is used by the logic of the FPGA 108 to set the transmit frequency. The low transistor (e.g., Low FET) Q2 turns ON at the beginning of the transmit period. The Low FET off value controls when the low transistor (e.g., Low FET) Q2 is turned OFF. The low transistor Q2 is turned OFF before the high transistor (e.g., High FET) Q1 is turned ON to avoid a short circuit through the transistors Q1, Q2. The High FET on value controls when the high transistor (e.g., High FET) Q1 is turned ON. The High FET Off value controls when the high transistor Q1 is turned OFF. The high transistor is turned OFF before the low transistor Q2 is turned ON to avoid a short circuit through the transistors Q1, Q2.

The ADC converts the signal received from the transponder 26, if any, from analog to digital. Such conversion may, for example, be performed at a sampling rate of 1 MHz with a 12-bit data resolution. The sampled ADC data is then accumulated together, for example over 400 pulses, to compute the total summed response signal received from the transponder 26, if any.

The accumulated received signal is match filtered with both in-phase and quadrature reference signals to determine the signal magnitude. Each of the four receive signals from the sequences shown are processed with three match filter frequencies, for example as shown in Table 1 below.

TABLE 1

| Sequence | Match Freq 1 | Match Freq 2 | Match Freq 3 |
|---|---|---|---|
| Noise | 139 KHz | 145 KHz | 151 KHz |
| 139 KHz | 136 KHz | 139 KHz | 142 KHz |
| 145 KHz | 142 KHz | 145 KHz | 148 KHz |
| 151 KHz | 148 KHz | 151 KHz | 154 KHz |

The maximum value for the nine matched filters with active transmit is compared with a fixed detection threshold. If the maximum value is greater than the detection threshold, then a response signal from a transponder 26 is considered as having been detected.

Figure 11:
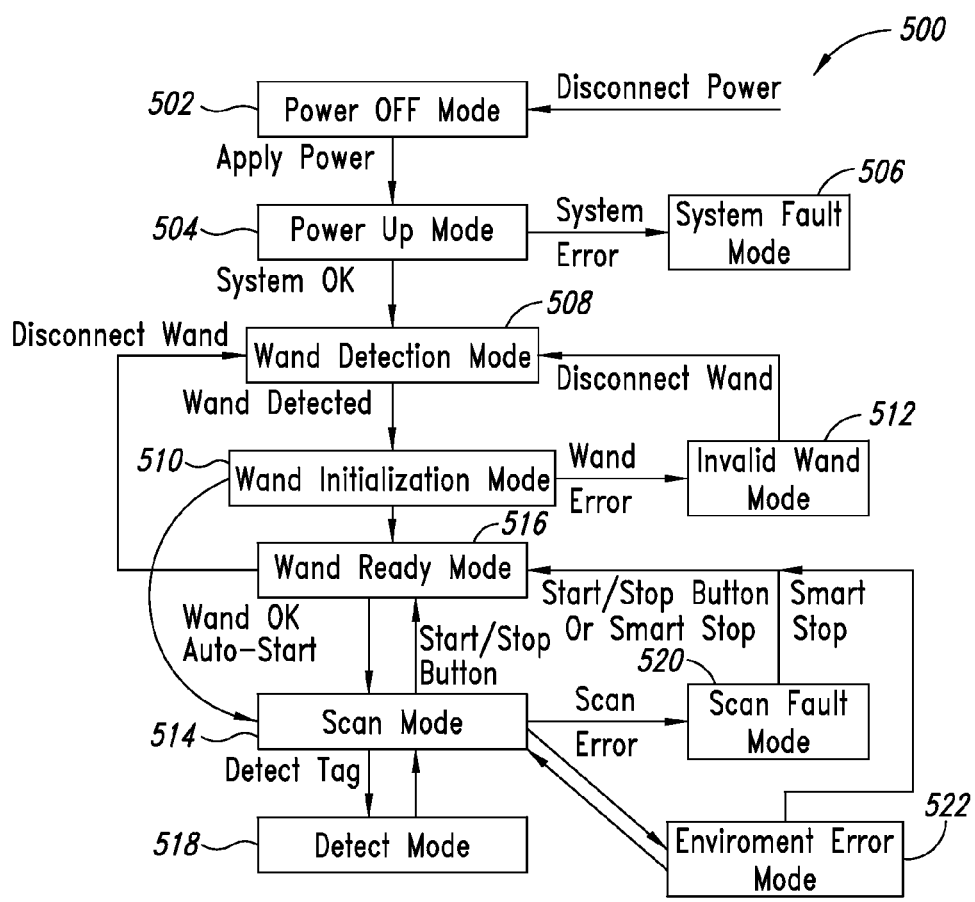
FIG. 11 is a flow diagram of a method of operating an interrogation and control system, according to one illustrated embodiment.

FIG. 11 shows a method 500 of operating the interrogation and detection system 14 according to one illustrated embodiment.

In response to detecting a disconnect of power, the interrogation and detection system 14 enters a Power OFF mode at 502. For example, the Power OFF mode 502 may be entered when the controller 20 (FIGS. 1 and 4) is unplugged or when the power switch on the controller 20 is turned OFF. In the Power OFF mode 502, the Power LED 134a and other front panel LEDs 134 will be turned OFF (non-emitting). The software 200 is inoperative in the Power OFF mode 502.

In response to detecting an application of power, the interrogation and detection system 14 enters a Power-Up mode 504. The Power UP mode 502 may, for example, in response to the application of power to the controller 20 and turning ON the switch on the back of the controller. In the Power-Up mode 504, a Power LED 134a may be turned ON or illuminated, and may remain ON or illuminated as long as the power is applied and the switch is in the ON state. In response to entering the Power UP mode 502, the software 200 will perform software initialization, built in tests, and an audio/visual test.

If a fault is detected, the software 200 progresses to a System Fault Mode 506. If no faults are detected, the software 200 may turn a System Ready LED green, and enter a Wand Detection Mode 508.

In the System Fault mode 506, the software 200 may cause an indication of the detection of a system fault by blinking a System Ready LED 134b yellow, and/or issuing a sequence of rapid beeps or other sounds. The corrective action for the System Fault Mode 506 is to cycle power to reinitiate the Power Up mode 504. Continued failure indicates a failed controller 20.

In the Wand Detection Mode 508, the software 200 checks for a wand 22a connected to the controller 20. The Wand Detection Mode 508 may be indicated by turning the System Ready LED 134b green and turning the Wand Ready LED 134c OFF. If no wand 22a is detected, the software 200 remains in the Wand Detection Mode. If a wand 22a is detected, the software 200 progresses to the Wand Initialization Mode 510.

At the start of the Wand Initialization Mode 510, after the detection of a wand 22a, the software 200 may turn the Wand Ready LED 134c yellow and check for the presence of a fuse in the wand 22a. If a fuse is found, the software 200 may attempt to blow the fuse and verify that the fuse was correctly blown. After the fuse is blown the software 200 may verify that wand 22a is operating within tolerances. The software 200 may indicate that the wand 22a is ready by turning the Wand Ready LED 134c green. The software 200 may also start a timer which will allow the wand 22a to be disconnected and reconnected to the controller for a period to time (e.g., 5 hours) after the fuse is blown.

The controller 20 may determine the adjustments or fine tuning to be made about the center frequencies or channels during Wand Initialization Mode 510. In particular, the controller 20 may determine the particular frequency in each of the frequency bands that elicits the response with the highest voltage. The controller may determine such be varying the capacitance of the LC circuit using the switched capacitors C33-C36 during the Wand Initialization Mode 510. The particular combination of switched capacitors C33-C36 which achieved the response with the highest voltage may then be automatically employed during the Scan Mode 514 (discussed below) to adjust or fine tune about the center frequency or channel in each broad band of transmission. Other approaches to determining the fine tuning may be employed.

If the software 200 does not successfully complete the Wand Initialization Mode 510, the software 200 enters an Invalid Wand Mode 512. If the software 200 successfully completes the Wand Initialization Mode 510, the software 200 progresses to the Scan Mode 514 to automatically start scanning.

In the Invalid Wand Mode 512, the software 200 may blink the Wand Ready LED 134c yellow and issues a slow beep pattern.

The Invalid Wand Mode may be entered in response to any of the following conditions:

The wand 22a connected to the controller 20 is out of tolerance.

The controller 20 is unable to blow the fuse in the wand 22a.

The wand 22a does not have a fuse and more than the set time period has past (e.g., 5 hours) since a fuse was blown.

The wand 22a does not have a fuse and the controller 20 has been restarted.

The wand 22a has been connected to the controller for more than the set time period (e.g., 5 hours).

The wand 22a is detuned due to close proximity to metal.

The corrective action for the Invalid Wand Mode 512 is to remove the invalid wand 22a and attach a new wand 22a to the controller 20 that contains a fuse or to reconnect the wand 22a while holding it in the air at least 2 feet away from large metallic objects.

The software 200 enters the Scan Mode 514 when the wand 22a is ready and the operator presses a Start/Stop button. The software 200 may issue a short three beep pattern via the speaker or beeper 130 when entering the Scan Mode 514 to identify the entry to the user.

In the Scan Mode 514, the software 200 may continuously or periodically perform the following functions.

Look for response signals from transponders 26
Monitor the noise level
Insure the wand 22a is connected and operating correctly
Blink the LED's in a circular pattern
When the operator or user pushes the Start/Stop button or the a scan maximum time interval (e.g., 4 minute) has been reached, the software 200 may issue a short three beep pattern and return to the Wand Ready Mode 516.

When an appropriate response signal from a transponder 26 is detected while in Scan Mode 514, the software 200 may turn ON an amber DETECT LEDs 134d and/or provide an audible alarm. The alarm may, for example, beep a continuous solid tone as long as the transponder is detected, with a minimum of beep duration of, for instance 0.5 second.

If the software 200 detects the wand 22a is disconnected while in the Scan Mode 514, the software 200 enter the Scan Fault Mode 520. In the Scan Fault Mode 520, the software 200 may issue a sequence of rapid beeps and blink ON and OFF the amber DETECT LEDs 134d. The Scan Fault Mode 520 can be cleared by pushing the Start/Stop button. The software 200 will automatically clear the scan fault mode 520 after 10 beeps.

While in the Scan Mode 514, if excess noise or loss of transmit signal is detected, the software 200 will progress to the Environment Error Mode 522. In the Environment Error Mode 522, the software 200 may issue or produce an appropriate indication. For example, the software 200 may cause the production of a sequence of slow beeps and the blinking ON and OFF the green circle LEDs 134e. The corrective action for the Environment Error Mode 522 is to reposition the wand 22a away from large metal objects or sources of electrical interference. The software 200 will automatically stop the scan if the environment error condition lasts for more than a set time or number of beeps (e.g., 5 beeps).

An alternative embodiment may significantly reduce or eliminate the chance of false positives. Such an embodiment may sample noise in a forward looking fashion in addition to a sample of noise in a backward looking fashion. The terms forward looking and backward looking are relative, being used relative to a given sample. The forward looking samples occur later in time than the given sample and the backward looking samples occur earlier in time than the given sample.

Figure 12:
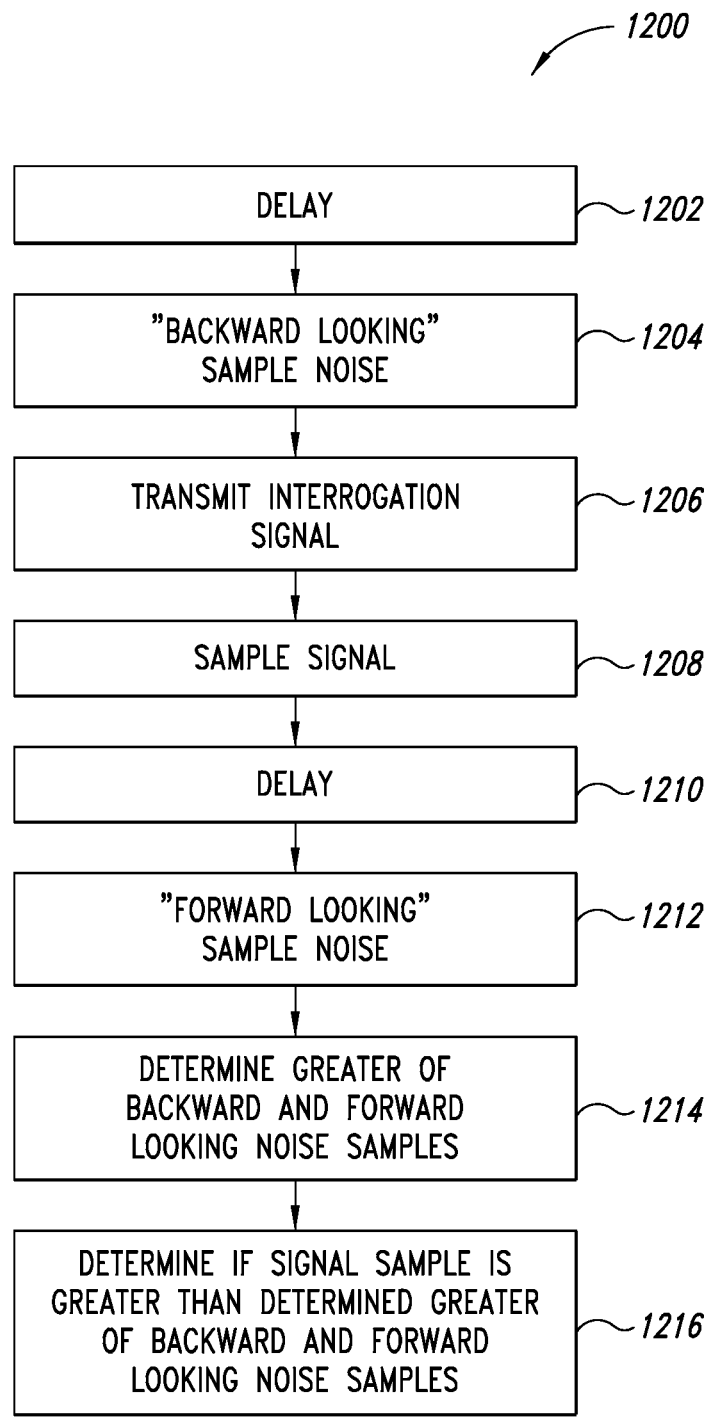
FIG. 12 is a flow diagram of a method of operating an interrogation and control system with reduced false positives, according to one illustrated embodiment.

FIG. 12 shows a method 1200 of operating an interrogation and control system with reduced false positives, according to one illustrated embodiment.

After a delay 1202, at 1204 a sample is taken at a first time sufficiently spaced by the delay in time 1202 from any prior interrogation signals such that the sample represents a "backward looking" noise sample. At 1206, an interrogation signal is transmitted. At 1208, a sample is taken at a second time sufficiently close to the interrogation signal such that the sample represents a signal sample, which may contain a return signal, if any, returned in response to the interrogation signal. After a delay 1210, at 1212 a "forward looking" sample is taken at third time, sufficiently spaced in time from the interrogation signal such that the sample represents a "forward looking" noise sample. At 1214, the greater of the backward looking and forward looking noise samples are determined. At 1216, the signal sample is compared with the determined greater one of the backward looking and forward looking noise samples to determine whether a response has been received from a transponder 26. An appropriate alert may be provided if a response has been received.

The method 1200 may advantageously address issues related to the fluctuation of the noise floor which may, for example, result from movement of the wand 22a. The duration of the signal sample may be longer than a duration of the noise samples, which will make the operation less sensitive to noise which, as previously noted, drops off as the square root of the sample.

The above description of illustrated embodiments, particularly the pulsed wide band frequency hopping with dynamic adjustment of the transmission frequency in the various frequency bands and the use of switched capacitors to achieve such, advantageously permit the use of inexpensive transponders which are not accurately tuned to a chosen or selected resonant frequency. This is in marked contrast to the approach typically taken with other types of resonant transponders (i.e., transponders without memory). Such approaches typically interrogate or excite the resonant transponder using narrow frequency bands centered closely on specific frequencies, to achieve a selected resonant response from a highly accurate transponder in order to differentiate signal from noise. This is also in marked contrast to the approach typically taken with radio frequency identification (RFID) tags whether active or passive, which also typically employ are narrow band to achieve a selected response from a highly accurate RFID tag.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Pat. No. 6,026,818, issued Feb. 22, 2000; U.S. Patent Publication No. US 2004/0250819, published Dec. 16, 2004; and U.S. provisional patent application Ser. No. 60/811,376, filed Jun. 6, 2006, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operating a transponder detection device, the method comprising:

responsive to communicably coupling an antenna circuit to the transponder detection device, automatically determining a first adjustment to spread energy across a first frequency band during a wand initialization mode, which includes determining a first tuning adjustment that increases an equalization of a spread of energy in the first frequency bank, the wand initialization mode preceding a scan mode during which the transponder detection device looks at a first time for a response to a signal transmitted in the respective first frequency band;

responsive to communicably coupling the antenna circuit to the transponder detection device, automatically determining a second adjustment to spread energy across a second frequency band, which includes determining a second tuning adjustment that increases an equalization of a spread of energy in the second frequency band;

transmitting a signal in the first frequency band during a first time;

transmitting a signal in the second frequency band during a second time;

receiving a response, if any, to the transmission of the signal in the first frequency band; and receiving a response, if any, to the transmission of the signal in the second frequency band.

2. The method of claim 1, further comprising:

setting a capacitance of a transmit circuit to a first capacitance value based on the first adjustment, before transmitting the signal in the first frequency band; and setting the capacitance of the transmit circuit to a second capacitance value based on the second adjustment, before transmitting the signal in the second frequency band.

3. The method of claim 2, further comprising:

dumping energy from an antenna circuit immediately after the transmitting of the signal in the first frequency band and before receiving a response, if any, to the transmission of the signal in the first frequency band; and dumping energy from the antenna circuit immediately following the transmitting of the signal in the second frequency band during the second time and before receiving a response, if any, to the transmission of the signal in the second frequency band.

4. The method of claim 3, further comprising:

providing a first recovery period between dumping energy from the antenna circuit immediately after the transmitting of the signal in the first frequency band and before receiving the response, if any, to the transmission of the signal in the first frequency band to allow a receiver circuit to recover from the transmitting of the signal in the first frequency band; and providing a second recovery period between dumping energy from the antenna circuit immediately after the transmitting of the signal in the second frequency band and before receiving the response, if any, to the transmission of the signal in the second frequency band to allow the receiver circuit to recover from the transmitting of the signal in the second frequency band.

5. The method of claim 1, further comprising:

responsive to communicably coupling of the antenna circuit to the transponder detection device, automatically determining a third adjustment to spread energy across a third frequency band;

transmitting a signal in the third frequency band during a third time; and receiving a response, if any, to the transmission of the signal in the third frequency band.

6. The method of claim 5 wherein automatically determining a first adjustment to spread energy across a first frequency band includes determining a first capacitance value that increases the equalization of a spread of energy in the first frequency band with respect to a non-adjusted spread of energy in the first frequency band, wherein automatically determining a second adjustment to spread energy across a second frequency band includes determining a second capacitance value that increases the equalization of a spread of energy in the second frequency band with respect to a non-adjusted spread of energy in the second frequency band, and wherein automatically determining a third adjustment to spread energy across a third frequency band includes determining a third capacitance value that increases an equalization of a spread of energy in the third frequency band with respect to a non-adjusted spread of energy in the third frequency band.

7. The method of claim 6, further comprising:

setting a capacitance of a transmit circuit to the first capacitance value before transmitting the signal in the first frequency band;

setting the capacitance of the transmit circuit to the second capacitance value before transmitting the signal in the second frequency band; and setting the capacitance of the transmit circuit to the third capacitance value before transmitting the signal in the third frequency band.

8. The method of claim 5, further comprising:

dumping energy from an antenna circuit immediately after the transmitting of the signal in the first frequency band and before receiving the response, if any, to the transmission of the signal in the first frequency band;

dumping energy from the antenna circuit immediately following the transmitting of the signal in the second frequency band during the second time and before receiving the response, if any, to the transmission of the signal in the second frequency band; and dumping energy from the antenna circuit immediately following the transmitting of the signal in the third frequency band during the third time and before receiving the response, if any, to the transmission of the signal in the third frequency band.

9. The method of claim 8, further comprising:

providing a first recovery period between dumping energy from the antenna driver circuit immediately after the transmitting of the signal in the first frequency band and before receiving the response, if any, to the transmission of the signal in the first frequency band to allow a receiver circuit to recover from the transmitting of the signal in the first frequency band;

providing a second recovery period between dumping energy from the antenna driver circuit immediately after the transmitting of the signal in the second frequency band and before receiving the response, if any, to the transmission of the signal in the second frequency band to allow the receiver circuit to recover from the transmitting of the signal in the second frequency band; and providing a third recovery period between dumping energy from the antenna driver circuit immediately after the transmitting of the signal in the third frequency band and before receiving the response, if any, to the transmission of the signal in the third frequency band to allow the receiver circuit to recover from the transmitting of the signal in the third frequency band.

10. The method of claim 5, further comprising:

repeatedly sequentially transmitting the signal in the first, the second and the third frequency bands.

11. The method of claim 10, further comprising:

varying an amount of time between successive repetitions of the repeated sequential transmitting of the signal in the first, the second and the third frequency bands.

12. The method of claim 5 wherein the second frequency band is different from the first frequency band, and the third frequency band is different from the first and the second frequency bands.

13. The method of claim 1 wherein transmitting includes operating a pair of field effect transistors in a push-pull arrangement to provide a pulsed signal on a coaxial transmission line coupled to an antenna with an adjustable capacitance to vary transmission about a respective center frequency of the frequency bands.

14. The method of claim 5 wherein automatically determining the first, the second, and the third adjustments occur during an initialization mode in response to detection of a new antenna being coupled to the device or a startup of the device.

15. A transponder detection device, comprising:
adjustment determination means for automatically determining, responsive to the communicable coupling of an antenna circuit to the transponder detection device, at least a first adjustment to spread energy across a first frequency band centered around a first center frequency during a wand initialization mode, the wand initialization mode preceding a scan mode during which the transponder detection device looks at a first time for a response to a signal transmitted in the respective first frequency band and a second adjustment to spread energy across a second frequency band centered around a second center frequency during the wand initialization mode preceding the scan mode during which the transponder detection device looks at a second time for a response to a signal transmitted in the respective second frequency band;
transmitting means for transmitting signals in at least the first frequency band during a first time and in the second frequency band during a second time;
adjusting means for increasing an equalization of the spread of energy across the first frequency band and the second frequency band in response to the adjustment determination means; and
receiving means for receiving a response, if any, from transponders, if any, to the transmissions of the signals in at least the first and the second frequency bands.

16. The transponder detection device of claim 15 wherein the adjusting means further determines at least a third adjustment to spread energy across a third frequency band centered around a third center frequency, the third frequency band different than the first and the second frequency bands, and the transmitting means transmits signals in at least the third frequency band, and the receiver means receives response, if any, from the transponders to the transmission of signals in at least the third frequency band.

17. The transponder detection device of claim 16 wherein the adjustment means includes a plurality of capacitors that are selectively switched into operation to vary a characteristic of an LC circuit including a transmission line.

18. The transponder detection device of claim 17, further comprising:
an antenna removeably coupled to the transmission line to form a low Q tuned LC circuit with the capacitors.

19. The transponder detection device of claim 16, further comprising:
dumping means for dumping energy from an antenna circuit immediately after the transmitting of the signals and before receiving the response, if any, to the transmission of the signals.

20. The transponder detection device of claim 19, further comprising:
recovery means for providing a recovery period between dumping energy from the antenna circuit and before receiving the response, if any, to the transmission of the signals.

21. The transponder detection device of claim 20, further comprising:
means for pseudo-randomly varying a time between transmission of signals in the first, the second and the third frequency bands and a successive transmission of signals in the first, the second and the third frequency bands.

22. A transponder detection device, comprising:
a transmitter circuit configured to produce signals in a plurality of frequency bands;
a dynamic tuning circuit coupled to the transmitter circuit and configured to, responsive to the communicable coupling of an antenna circuit to the transponder detection device, tune about a respective center channel within each of the plurality of frequency bands to increase an equalization of a distribution of energy in the respective frequency band during a wand initialization mode, the wand initialization mode preceding a scan mode during which the transponder detection device looks at a plurality of respective times for a response to a signal transmitted in each of the respective plurality of frequency bands; and
a receiver circuit configured to receive signals returned by a transponder in response to the signals in the plurality of frequency bands.

23. The transponder detection device of claim 22, further comprising:
a transmission line.

24. The transponder detection device of claim 23 wherein the transmitter circuit includes a pair of transistors electrically coupled in push-pull configuration and operable to produce a pulse signal on the transmission line.

25. The transponder detection device of claim 24, wherein the antenna circuit is removeably coupled to the transmission line.

26. The transponder detection device of claim 25 wherein the dynamic tuning circuit includes a plurality of switched capacitors to form a low Q tuned LC circuit with the antenna, the switched capacitors configured to vary an LC characteristic of the LC circuit formed by at least the antenna and the switched capacitors.

27. The transponder detection device of claim 22 wherein the Q factor of the low Q tuned LC circuit formed by at least the antenna and the switched capacitors is less than about 12.

28. The transponder detection device of claim 22 wherein the dynamic tuning circuit includes a non-switched capacitor and a plurality of switched capacitors configured to vary a transmission characteristic of an antenna circuit.

29. The transponder device of claim 22 wherein the dynamic tuning circuit is configured to determine a first capacitance value that increases the equalization of the distribution of energy in a first frequency band with respect to a non-adjusted distribution of energy in the first frequency band associated with the center channel of the first frequency band, determine a second capacitance value that increases the equalization of distribution of energy in the second frequency band with respect to a non-adjusted distribution of energy in the second frequency band associated with the center channel of the second frequency band, and determines a third capacitance value that increases the equalization of the distribution of energy in the third frequency band with respect to a non-adjusted distribution of energy in the third frequency band associated with the center channel of the third frequency band.

30. A method of operating a transponder detection device, the method comprising:

obtaining a backward looking noise sample during a first time;

transmitting an interrogation signal in a first frequency band during a second time;

obtaining a signal sample at a second time sufficiently close in time to the interrogation signal such that the obtained signal sample represents a return signal, if any, returned in response to the interrogation signal;

obtaining a forward looking noise sample during a third time sufficiently spaced in time from the transmitting of the interrogation signal such that the forward looking sample does not represent the return signal, if any, returned in response to the interrogation signal; and comparing the signal sample to a greater of the forward and the backward looking noise samples to determine whether the signal sample contains the return signal.

31. The method of claim 30, the method further comprising:

producing an alert if a magnitude of the signal sample is greater than the greater of the forward and the backward looking noise samples.

32. The method of claim 30, the method further comprising:

transmitting an interrogation signal in a second frequency band during a fourth time;

obtaining a signal sample at a fifth time sufficiently close in time to the interrogation signal such that the obtained signal sample represents a return signal, if any, returned in response to the interrogation signal;

obtaining a forward looking noise sample during a sixth time sufficiently spaced in time from the transmitting of the interrogation signal such that the forward looking sample does not represent the return signal, if any, returned in response to the interrogation signal; and comparing the signal sample to a greater of the forward looking noise samples taken at the third and the sixth times to determine whether the sample signal contains the return signal.

33. A method of operating a transponder detection device, the method comprising:

automatically adjusting at least one antenna circuit parameter to elicit a peak voltage response at a first center frequency and automatically determining a first adjustment to an antenna circuit to increase the equalization of a spread of energy across a first frequency band about the first center frequency during a wand initialization mode, the wand initialization mode preceding a scan mode during which the transponder detection device looks at a first time for a response to a signal transmitted in the respective first frequency band;

automatically adjusting the at least one antenna circuit parameter to elicit a peak voltage response at a second center frequency and automatically determining a second adjustment to the antenna circuit to increase the equalization of a spread of energy across a second frequency band about the second center frequency during the wand initialization mode preceding the scan mode during which the transponder detection device looks at a second time for a response to a signal transmitted in the respective second frequency band;

responsive to the equalization of the spread of energy across the first frequency band and to the equalization of the spread of energy across the second frequency band, transmitting a plurality of signals in the first frequency band during at least one first time interval and transmitting a plurality of signals in the second frequency band during at least one second time interval;

receiving the response, if any, to the transmission of the signal in the first frequency band; and receiving the response, if any, to the transmission of the signal in the second frequency band.

34. The method of claim 33, further comprising:

communicably coupling an antenna circuit to the transponder detection device;

wherein automatically adjusting at least one antenna circuit parameter to elicit a peak voltage response at a first center frequency and automatically adjusting the at least one antenna circuit parameter to elicit a peak voltage response at a second center frequency occurs autonomously, responsive to the communicable coupling of the antenna circuit to the transponder detection device.

35. The method of claim 1 wherein automatically determining a second adjustment to spread energy across a second frequency band comprises:

determining a second tuning adjustment that increases an equalization of a spread of energy in the second frequency band during the wand initialization mode preceding the scan mode during which the transponder detection device looks at a second time for a response to a signal transmitted in the respective second frequency band.

* * * * *

UNITED STATES PATENT AND TRADEMARK OFFICE
CERTIFICATE OF CORRECTION

PATENT NO. : 8,710,957 B2
APPLICATION NO. : 12/038593
DATED : April 29, 2014
INVENTOR(S) : William A. Blair et al.

It is certified that error appears in the above-identified patent and that said Letters Patent is hereby corrected as shown below:

In the claims

Column 14, Line 67, Claim 1:
"first frequency bank, the wand initialization mode" should read, --first frequency band, the wand initialization mode--.

Signed and Sealed this
Eighth Day of December, 2015

Michelle K. Lee
*Director of the United States Patent and Trademark Office*